US012765808B2

(12) United States Patent
Zade et al.

(10) Patent No.: US 12,765,808 B2
(45) Date of Patent: Oct. 20, 2026

(54) TECHNIQUES FOR IMAGE-BASED MONITORING OF BLOOD GLUCOSE STATUS

(71) Applicant: Insulet Corporation, Acton, MA (US)

(72) Inventors: Ashutosh Zade, San Diego, CA (US); Joon Bok Lee, Acton, MA (US); Yibin Zheng, Hartland, WI (US); Steven Cardinali, Tewksbury, MA (US)

(73) Assignee: INSULET CORPORATION, Acton, MA (US)

( * ) Notice: Subject to any disclaimer, the term of this patent is extended or adjusted under 35 U.S.C. 154(b) by 881 days.

(21) Appl. No.: 17/003,854

(22) Filed: Aug. 26, 2020

(65) Prior Publication Data

US 2022/0061706 A1 Mar. 3, 2022

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/4839* (2013.01); *A61B 5/4848* (2013.01);
(Continued)

(58) Field of Classification Search
CPC . A61B 5/14532; A61B 5/4839; A61B 5/4848; A61B 5/7221; A61B 5/7264;
(Continued)

(56) References Cited

U.S. PATENT DOCUMENTS

| | | | |
|---|---|---|---|
| 303,013 | A | 8/1884 | Horton |
| 2,797,149 | A | 6/1957 | Skeggs |

(Continued)

FOREIGN PATENT DOCUMENTS

| | | | |
|---|---|---|---|
| AU | 2015200834 | A1 | 3/2015 |
| AU | 2015301146 | A1 | 3/2017 |

(Continued)

OTHER PUBLICATIONS

US 5,954,699 A, 09/1999, Jost et al. (withdrawn)
(Continued)

*Primary Examiner* — Michael J Tsai
*Assistant Examiner* — Neeraja Gollamudi
(74) *Attorney, Agent, or Firm* — Goodwin Procter LLP

(57) ABSTRACT

Methods and apparatuses for performing a blood glucose monitoring process are described. For example, an apparatus may include at least one memory and logic coupled to the at least one memory. The logic may operate to determine patient monitoring information associated with a diabetic treatment of a patient, generate at least one monitoring information structure based on the patient monitoring information, generate at least one monitoring information image based on at least a portion of the at least one monitoring information structure, and process the at least one monitoring information image using a computational model to determine a blood glucose condition of the patient. Other embodiments are described.

8 Claims, 11 Drawing Sheets

(51) Int. Cl.
*A61K 38/28* (2006.01)
*A61M 5/172* (2006.01)
*A61M 5/142* (2006.01)

(52) U.S. Cl.
CPC .......... *A61B 5/7221* (2013.01); *A61B 5/7264* (2013.01); *A61B 5/7275* (2013.01); *A61B 5/7282* (2013.01); *A61B 5/743* (2013.01); *A61K 38/28* (2013.01); *A61M 5/1723* (2013.01); *A61M 5/14248* (2013.01); *A61M 2205/18* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2230/201* (2013.01)

(58) Field of Classification Search
CPC ..... A61B 5/7275; A61B 5/743; A61B 5/7282; A61M 5/1723; A61M 2205/52; A61M 2230/201
See application file for complete search history.

(56) References Cited

U.S. PATENT DOCUMENTS 3,631,847 A 1/1972 Hobbs
3,634,039 A 1/1972 Brondy
3,812,843 A 5/1974 Wootten et al.
3,841,328 A 10/1974 Jensen
3,963,380 A 6/1976 Thomas, Jr. et al.
4,055,175 A 10/1977 Clemens et al.
4,146,029 A 3/1979 Ellinwood, Jr.
4,151,845 A 5/1979 Clemens
4,245,634 A 1/1981 Albisser et al.
4,368,980 A 1/1983 Aldred et al.
4,373,527 A 2/1983 Fischell
4,403,984 A 9/1983 Ash et al.
4,464,170 A 8/1984 Clemens et al.
4,469,481 A 9/1984 Kobayashi
4,475,901 A 10/1984 Kraegen et al.
4,526,568 A 7/1985 Clemens et al.
4,526,569 A 7/1985 Bernardi
4,529,401 A 7/1985 Leslie et al.
4,559,033 A 12/1985 Stephen et al.
4,559,037 A 12/1985 Franetzki et al.
4,573,968 A 3/1986 Parker
4,624,661 A 11/1986 Arimond
4,633,878 A 1/1987 Bombardieri
4,657,529 A 4/1987 Prince et al.
4,685,903 A 8/1987 Cable et al.
4,731,726 A 3/1988 Allen, III
4,743,243 A 5/1988 Vaillancourt
4,755,173 A 7/1988 Konopka et al.
4,781,688 A 11/1988 Thoma et al.
4,781,693 A 11/1988 Martinez et al.
4,808,161 A 2/1989 Kamen
4,854,170 A 8/1989 Brimhall et al.
4,886,499 A 12/1989 Cirelli et al.
4,900,292 A 2/1990 Berry et al.
4,919,596 A 4/1990 Slate et al.
4,925,444 A 5/1990 Orkin et al.
4,940,527 A 7/1990 Kazlauskas et al.
4,975,581 A 12/1990 Robinson et al.
4,976,720 A 12/1990 Machold et al.
4,981,140 A 1/1991 Wyatt
4,994,047 A 2/1991 Walker et al.
5,007,286 A 4/1991 Malcolm et al.
5,097,834 A 3/1992 Skrabal
5,102,406 A 4/1992 Arnold
5,109,850 A 5/1992 Blanco et al.
5,125,415 A 6/1992 Bell
5,134,079 A 7/1992 Cusack et al.
5,153,827 A 10/1992 Coutre et al.
5,165,406 A 11/1992 Wong
5,176,662 A 1/1993 Bartholomew et al.
5,178,609 A 1/1993 Ishikawa
5,207,642 A 5/1993 Orkin et al.
5,232,439 A 8/1993 Campbell et al.
5,237,993 A 8/1993 Skrabal
5,244,463 A 9/1993 Cordner, Jr. et al.
5,257,980 A 11/1993 Van Antwerp et al.
5,273,517 A 12/1993 Barone et al.
5,281,808 A 1/1994 Kunkel
5,299,571 A 4/1994 Mastrototaro
5,308,982 A 5/1994 Ivaldi et al.
5,342,298 A 8/1994 Michaels et al.
5,377,674 A 1/1995 Kuestner
5,380,665 A 1/1995 Cusack et al.
5,385,539 A 1/1995 Maynard
5,389,078 A 2/1995 Zalesky
5,411,889 A 5/1995 Hoots et al.
5,421,812 A 6/1995 Langley et al.
5,468,727 A 11/1995 Phillips et al.
5,505,709 A 4/1996 Funderburk et al.
5,505,828 A 4/1996 Wong et al.
5,507,288 A 4/1996 Bocker et al.
5,533,389 A 7/1996 Kamen et al.
5,558,640 A 9/1996 Pfeiler et al.
5,569,186 A 10/1996 Lord et al.
5,584,813 A 12/1996 Livingston et al.
5,609,572 A 3/1997 Lang
5,665,065 A 9/1997 Colman et al.
5,678,539 A 10/1997 Schubert et al.
5,685,844 A 11/1997 Marttila
5,685,859 A 11/1997 Kornerup
5,693,018 A 12/1997 Kriesel et al.
5,697,899 A 12/1997 Hillman et al.
5,700,695 A 12/1997 Yassinzadeh et al.
5,703,364 A 12/1997 Rosenthal
5,714,123 A 2/1998 Sohrab
5,716,343 A 2/1998 Kriesel et al.
5,722,397 A 3/1998 Eppstein
5,741,228 A 4/1998 Lambrecht et al.
5,746,217 A 5/1998 Erickson et al.
5,755,682 A 5/1998 Knudson et al.
5,758,643 A 6/1998 Wong et al.
5,800,405 A 9/1998 McPhee
5,800,420 A 9/1998 Gross et al.
5,801,057 A 9/1998 Smart et al.
5,804,048 A 9/1998 Wong et al.
5,817,007 A 10/1998 Fodgaard et al.
5,820,622 A 10/1998 Gross et al.
5,823,951 A 10/1998 Messerschmidt
5,840,020 A 11/1998 Heinonen et al.
5,848,991 A 12/1998 Gross et al.
5,851,197 A 12/1998 Marano et al.
5,858,005 A 1/1999 Kriesel
5,865,806 A 2/1999 Howell
5,871,470 A 2/1999 McWha
5,879,310 A 3/1999 Sopp et al.
5,902,253 A 5/1999 Pfeiffer et al.
5,931,814 A 8/1999 Alex et al.
5,932,175 A 8/1999 Knute et al.
5,935,099 A 8/1999 Peterson et al.
5,947,911 A 9/1999 Wong et al.
5,971,941 A 10/1999 Simons et al.
5,993,423 A 11/1999 Choi
5,997,501 A 12/1999 Gross et al.
6,017,318 A 1/2000 Gauthier et al.
6,024,539 A 2/2000 Blomquist
6,032,059 A 2/2000 Henning et al.
6,036,924 A 3/2000 Simons et al.
6,040,578 A 3/2000 Malin et al.
6,049,727 A 4/2000 Crothall
6,050,978 A 4/2000 Orr et al.
6,058,934 A 5/2000 Sullivan
6,066,103 A 5/2000 Duchon et al.
6,071,292 A 6/2000 Makower et al.
6,072,180 A 6/2000 Kramer et al.
6,077,055 A 6/2000 Vilks
6,090,092 A 7/2000 Fowles et al.
6,101,406 A 8/2000 Hacker et al.
6,102,872 A 8/2000 Doneen et al.

(56) References Cited

U.S. PATENT DOCUMENTS 6,115,673 A * 9/2000 Malin .................. G01N 21/274
702/30
6,123,827 A 9/2000 Wong et al.
6,124,134 A 9/2000 Stark
6,126,637 A 10/2000 Kriesel et al.
6,128,519 A 10/2000 Say
6,142,939 A 11/2000 Eppstein et al.
6,143,164 A 11/2000 Heller et al.
6,157,041 A 12/2000 Thomas et al.
6,161,028 A 12/2000 Braig et al.
6,162,639 A 12/2000 Douglas
6,196,046 B1 3/2001 Braig et al.
6,200,287 B1 3/2001 Keller et al.
6,200,338 B1 3/2001 Solomon et al.
6,214,629 B1 4/2001 Freitag et al.
6,226,082 B1 5/2001 Roe
6,244,776 B1 6/2001 Wiley
6,261,065 B1 7/2001 Nayak et al.
6,262,798 B1 7/2001 Shepherd et al.
6,270,455 B1 8/2001 Brown
6,271,045 B1 8/2001 Douglas et al.
6,280,381 B1 8/2001 Malin et al.
6,285,448 B1 9/2001 Kuenstner
6,309,370 B1 10/2001 Haim et al.
6,312,888 B1 11/2001 Wong et al.
6,334,851 B1 1/2002 Hayes et al.
6,375,627 B1 4/2002 Mauze et al.
6,379,301 B1 4/2002 Worthington et al.
6,402,689 B1 6/2002 Scarantino et al.
6,470,279 B1 10/2002 Samsoondar
6,475,196 B1 11/2002 Vachon
6,477,901 B1 11/2002 Tadigadapa et al.
6,484,044 B1 11/2002 Lilienfeld-Toal
6,491,656 B1 12/2002 Morris
6,512,937 B2 1/2003 Blank et al.
6,525,509 B1 2/2003 Petersson et al.
6,528,809 B1 3/2003 Thomas et al.
6,540,672 B1 4/2003 Simonsen et al.
6,544,212 B2 4/2003 Galley et al.
6,546,268 B1 4/2003 Ishikawa et al.
6,546,269 B1 4/2003 Kurnik
6,553,841 B1 4/2003 Blouch
6,554,798 B1 4/2003 Mann et al.
6,556,850 B1 4/2003 Braig et al.
6,558,351 B1 5/2003 Steil et al.
6,560,471 B1 5/2003 Heller et al.
6,561,978 B1 5/2003 Conn et al.
6,562,001 B2 5/2003 Lebel et al.
6,562,014 B2 5/2003 Lin et al.
6,569,125 B2 5/2003 Jepson et al.
6,572,542 B1 6/2003 Houben et al.
6,572,545 B2 6/2003 Knobbe et al.
6,574,490 B2 6/2003 Abbink et al.
6,575,905 B2 6/2003 Knobbe et al.
6,580,934 B1 6/2003 Braig et al.
6,618,603 B2 9/2003 Varalli et al.
6,633,772 B2 10/2003 Ford et al.
6,645,142 B2 11/2003 Braig et al.
6,653,091 B1 11/2003 Dunn et al.
6,662,030 B2 12/2003 Khalil et al.
6,669,663 B1 12/2003 Thompson
6,678,542 B2 1/2004 Braig et al.
6,699,221 B2 3/2004 Vaillancourt
6,718,189 B2 4/2004 Rohrscheib et al.
6,721,582 B2 4/2004 Trepagnier et al.
6,728,560 B2 4/2004 Kollias et al.
6,740,059 B2 5/2004 Flaherty
6,740,072 B2 5/2004 Starkweather et al.
6,751,490 B2 6/2004 Esenaliev et al.
6,758,835 B2 7/2004 Close et al.
6,780,156 B2 8/2004 Haueter et al.
6,810,290 B2 10/2004 Lebel et al.
6,837,858 B2 1/2005 Cunningham et al.
6,837,988 B2 1/2005 Leong et al.
6,846,288 B2 1/2005 Nagar et al.
6,862,534 B2 3/2005 Sterling et al.
6,865,408 B1 3/2005 Abbink et al.
6,890,291 B2 5/2005 Robinson et al.
6,936,029 B2 8/2005 Mann et al.
6,949,081 B1 9/2005 Chance
6,958,809 B2 10/2005 Sterling et al.
6,989,891 B2 1/2006 Braig et al.
6,990,366 B2 1/2006 Say et al.
7,008,404 B2 3/2006 Nakajima
7,009,180 B2 3/2006 Sterling et al.
7,016,713 B2 3/2006 Gardner et al.
7,018,360 B2 3/2006 Flaherty et al.
7,025,743 B2 4/2006 Mann et al.
7,025,744 B2 4/2006 Utterberg et al.
7,027,848 B2 4/2006 Robinson et al.
7,043,288 B2 5/2006 Davis, III et al.
7,060,059 B2 6/2006 Keith et al.
7,061,593 B2 6/2006 Braig et al.
7,096,124 B2 8/2006 Sterling et al.
7,115,205 B2 10/2006 Robinson et al.
7,128,727 B2 10/2006 Flaherty et al.
7,139,593 B2 11/2006 Kavak et al.
7,139,598 B2 11/2006 Hull et al.
7,144,384 B2 12/2006 Gorman et al.
7,171,252 B1 1/2007 Scarantino et al.
7,190,988 B2 3/2007 Say et al.
7,204,823 B2 4/2007 Estes et al.
7,248,912 B2 7/2007 Gough et al.
7,267,665 B2 9/2007 Steil et al.
7,271,912 B2 9/2007 Sterling et al.
7,278,983 B2 10/2007 Ireland et al.
7,291,107 B2 11/2007 Hellwig et al.
7,291,497 B2 11/2007 Holmes et al.
7,303,549 B2 12/2007 Flaherty et al.
7,303,622 B2 12/2007 Loch et al.
7,303,922 B2 12/2007 Jeng et al.
7,354,420 B2 4/2008 Steil et al.
7,388,202 B2 6/2008 Sterling et al.
7,402,153 B2 7/2008 Steil et al.
7,404,796 B2 7/2008 Ginsberg
7,429,255 B2 9/2008 Thompson
7,460,130 B2 12/2008 Salganicoff
7,481,787 B2 1/2009 Gable et al.
7,491,187 B2 2/2009 Van Den Berghe et al.
7,500,949 B2 3/2009 Gottlieb et al.
7,509,156 B2 3/2009 Flanders
7,547,281 B2 6/2009 Hayes et al.
7,569,030 B2 8/2009 Lebel et al.
7,608,042 B2 10/2009 Goldberger et al.
7,651,845 B2 1/2010 Doyle, III et al.
7,680,529 B2 3/2010 Kroll
7,734,323 B2 6/2010 Blomquist et al.
7,766,829 B2 8/2010 Sloan et al.
7,785,258 B2 8/2010 Braig et al.
7,806,854 B2 10/2010 Damiano et al.
7,806,886 B2 10/2010 Kanderian, Jr. et al.
7,918,825 B2 4/2011 OConnor et al.
7,946,985 B2 5/2011 Mastrototaro et al.
7,972,296 B2 7/2011 Braig et al.
8,221,345 B2 7/2012 Blomquist
8,251,907 B2 8/2012 Sterling et al.
8,449,524 B2 5/2013 Braig et al.
8,452,359 B2 5/2013 Rebec et al.
8,454,576 B2 6/2013 Mastrototaro et al.
8,467,980 B2 6/2013 Campbell et al.
8,478,557 B2 7/2013 Hayter et al.
8,547,239 B2 10/2013 Peatfield et al.
8,597,274 B2 12/2013 Sloan et al.
8,622,988 B2 1/2014 Hayter
8,810,394 B2 8/2014 Kalpin
9,061,097 B2 6/2015 Holt et al.
9,171,343 B1 10/2015 Fischell et al.
9,233,204 B2 1/2016 Booth et al.
9,486,571 B2 11/2016 Rosinko et al.
9,579,456 B2 2/2017 Budiman et al.
9,743,224 B2 8/2017 San Vicente et al.
9,907,515 B2 3/2018 Doyle, III et al.
9,980,140 B1 5/2018 Spencer et al.
9,984,773 B2 5/2018 Gondhalekar et al.

(56) References Cited

U.S. PATENT DOCUMENTS 10,248,839 B2 4/2019 Levy et al.
10,583,250 B2 3/2020 Mazlish et al.
10,737,024 B2 8/2020 Schmid
10,987,468 B2 4/2021 Mazlish et al.
11,197,964 B2 12/2021 Sjolund et al.
11,260,169 B2 3/2022 Estes
2001/0021803 A1 9/2001 Blank et al.
2001/0034023 A1 10/2001 Stanton, Jr. et al.
2001/0034502 A1 10/2001 Moberg et al.
2001/0051377 A1 12/2001 Hammer et al.
2001/0053895 A1 12/2001 Vaillancourt
2002/0010401 A1 1/2002 Bushmakin et al.
2002/0010423 A1 1/2002 Gross et al.
2002/0016568 A1 2/2002 Lebel et al.
2002/0040208 A1 4/2002 Flaherty et al.
2002/0123740 A1 9/2002 Flaherty et al.
2002/0128543 A1 9/2002 Leonhardt
2002/0147423 A1 10/2002 Burbank et al.
2002/0155425 A1 10/2002 Han et al.
2002/0161288 A1 10/2002 Shin et al.
2003/0023148 A1 1/2003 Lorenz et al.
2003/0050621 A1 3/2003 Lebel et al.
2003/0060692 A1 3/2003 Ruchti et al.
2003/0086074 A1 5/2003 Braig et al.
2003/0086075 A1 5/2003 Braig et al.
2003/0090649 A1 5/2003 Sterling et al.
2003/0100040 A1 5/2003 Bonnecaze et al.
2003/0130616 A1* 7/2003 Steil .................... A61B 5/1495 600/365
2003/0135388 A1 7/2003 Martucci et al.
2003/0144582 A1 7/2003 Cohen et al.
2003/0163097 A1 8/2003 Fleury et al.
2003/0195404 A1 10/2003 Knobbe et al.
2003/0208113 A1 11/2003 Mault et al.
2003/0208154 A1 11/2003 Close et al.
2003/0212379 A1 11/2003 Bylund et al.
2003/0216627 A1 11/2003 Lorenz et al.
2003/0220605 A1 11/2003 Bowman, Jr. et al.
2004/0010207 A1 1/2004 Flaherty et al.
2004/0034295 A1 2/2004 Salganicoff
2004/0045879 A1 3/2004 Shults et al.
2004/0051368 A1 3/2004 Caputo et al.
2004/0064259 A1 4/2004 Haaland et al.
2004/0097796 A1 5/2004 Berman et al.
2004/0116847 A1 6/2004 Wall
2004/0122353 A1 6/2004 Shahmirian et al.
2004/0133166 A1 7/2004 Moberg et al.
2004/0147034 A1 7/2004 Gore et al.
2004/0171983 A1 9/2004 Sparks et al.
2004/0203357 A1 10/2004 Nassimi
2004/0204868 A1 10/2004 Maynard et al.
2004/0215492 A1 10/2004 Choi
2004/0220517 A1 11/2004 Starkweather et al.
2004/0241736 A1 12/2004 Hendee et al.
2004/0249308 A1 12/2004 Forssell
2005/0003470 A1 1/2005 Nelson et al.
2005/0020980 A1 1/2005 Inoue et al.
2005/0022274 A1 1/2005 Campbell et al.
2005/0033148 A1 2/2005 Haueter et al.
2005/0049179 A1 3/2005 Davidson et al.
2005/0065464 A1 3/2005 Talbot et al.
2005/0065465 A1 3/2005 Lebel et al.
2005/0075624 A1 4/2005 Miesel
2005/0105095 A1 5/2005 Pesach et al.
2005/0137573 A1 6/2005 McLaughlin
2005/0171503 A1 8/2005 Van Den Berghe et al.
2005/0182306 A1 8/2005 Sloan
2005/0192494 A1 9/2005 Ginsberg
2005/0192557 A1 9/2005 Brauker et al.
2005/0197621 A1 9/2005 Poulsen et al.
2005/0203360 A1 9/2005 Brauker et al.
2005/0203461 A1 9/2005 Flaherty et al.
2005/0238507 A1 10/2005 Dilanni et al.
2005/0261660 A1 11/2005 Choi
2005/0272640 A1 12/2005 Doyle, III et al.
2005/0277912 A1 12/2005 John
2006/0009727 A1 1/2006 OMahony et al.
2006/0079809 A1 4/2006 Goldberger et al.
2006/0100494 A1 5/2006 Kroll
2006/0134323 A1 6/2006 OBrien
2006/0167350 A1 7/2006 Monfre et al.
2006/0173406 A1 8/2006 Hayes et al.
2006/0189925 A1 8/2006 Gable et al.
2006/0189926 A1 8/2006 Hall et al.
2006/0197015 A1 9/2006 Sterling et al.
2006/0200070 A1 9/2006 Callicoat et al.
2006/0204535 A1 9/2006 Johnson
2006/0229531 A1 10/2006 Goldberger et al.
2006/0253085 A1 11/2006 Geismar et al.
2006/0264895 A1 11/2006 Flanders
2006/0270983 A1 11/2006 Lord et al.
2006/0276771 A1 12/2006 Galley et al.
2006/0282290 A1 12/2006 Flaherty et al.
2007/0016127 A1 1/2007 Staib et al.
2007/0060796 A1 3/2007 Kim
2007/0060869 A1 3/2007 Tolle et al.
2007/0060872 A1 3/2007 Hall et al.
2007/0083160 A1 4/2007 Hall et al.
2007/0106135 A1 5/2007 Sloan et al.
2007/0116601 A1 5/2007 Patton
2007/0118405 A1 5/2007 Campbell et al.
2007/0129690 A1 6/2007 Rosenblatt et al.
2007/0142720 A1 6/2007 Ridder et al.
2007/0173761 A1 7/2007 Kanderian et al.
2007/0173974 A1 7/2007 Lin
2007/0179352 A1 8/2007 Randlov et al.
2007/0191716 A1 8/2007 Goldberger et al.
2007/0197163 A1 8/2007 Robertson
2007/0225675 A1 9/2007 Robinson et al.
2007/0244381 A1 10/2007 Robinson et al.
2007/0249007 A1 10/2007 Rosero
2007/0264707 A1 11/2007 Liederman et al.
2007/0282269 A1 12/2007 Carter et al.
2007/0287985 A1 12/2007 Estes et al.
2007/0293843 A1 12/2007 Ireland et al.
2008/0033272 A1 2/2008 Gough et al.
2008/0051764 A1 2/2008 Dent et al.
2008/0058625 A1 3/2008 McGarraugh et al.
2008/0065050 A1 3/2008 Sparks et al.
2008/0071157 A1 3/2008 McGarraugh et al.
2008/0071158 A1 3/2008 McGarraugh et al.
2008/0078400 A1 4/2008 Martens et al.
2008/0092638 A1* 4/2008 Brenneman ............ G16H 10/40 73/61.41
2008/0097289 A1 4/2008 Steil et al.
2008/0132880 A1 6/2008 Buchman
2008/0161664 A1 7/2008 Mastrototaro et al.
2008/0172026 A1 7/2008 Blomquist
2008/0177165 A1 7/2008 Blomquist et al.
2008/0188796 A1 8/2008 Steil et al.
2008/0200838 A1 8/2008 Goldberger et al.
2008/0206067 A1 8/2008 De Corral et al.
2008/0208113 A1 8/2008 Damiano et al.
2008/0214919 A1 9/2008 Harmon et al.
2008/0228056 A1 9/2008 Blomquist et al.
2008/0249386 A1 10/2008 Besterman et al.
2008/0269585 A1 10/2008 Ginsberg
2008/0269714 A1 10/2008 Mastrototaro et al.
2008/0269723 A1 10/2008 Mastrototaro et al.
2008/0287906 A1 11/2008 Burkholz et al.
2009/0006061 A1 1/2009 Thukral et al.
2009/0018406 A1 1/2009 Yodfat et al.
2009/0030398 A1 1/2009 Yodfat et al.
2009/0036753 A1 2/2009 King
2009/0043240 A1 2/2009 Robinson et al.
2009/0054753 A1 2/2009 Robinson et al.
2009/0069743 A1 3/2009 Krishnamoorthy et al.
2009/0069745 A1 3/2009 Estes et al.
2009/0069787 A1 3/2009 Estes et al.
2009/0099521 A1 4/2009 Gravesen et al.
2009/0105573 A1 4/2009 Malecha
2009/0131861 A1 5/2009 Braig et al.
2009/0156922 A1 6/2009 Goldberger et al.
2009/0156924 A1 6/2009 Shariati et al.

(56) References Cited

U.S. PATENT DOCUMENTS

2009/0163781 A1 6/2009 Say et al.
2009/0198350 A1 8/2009 Thiele
2009/0221890 A1 9/2009 Saffer et al.
2009/0228214 A1 9/2009 Say et al.
2009/0318791 A1 12/2009 Kaastrup
2009/0326343 A1 12/2009 Gable et al.
2010/0057042 A1 3/2010 Hayter
2010/0114026 A1 5/2010 Karratt et al.
2010/0121170 A1 5/2010 Rule
2010/0137784 A1 6/2010 Cefai et al.
2010/0152658 A1 6/2010 Hanson et al.
2010/0174228 A1 7/2010 Buckingham et al.
2010/0211003 A1 8/2010 Sundar et al.
2010/0228110 A1 9/2010 Tsoukalis
2010/0262117 A1 10/2010 Magni et al.
2010/0262434 A1 10/2010 Shaya
2010/0295686 A1 11/2010 Sloan et al.
2010/0298765 A1 11/2010 Budiman et al.
2011/0021584 A1 1/2011 Berggren et al.
2011/0028817 A1 2/2011 Jin et al.
2011/0054390 A1 3/2011 Searle et al.
2011/0054399 A1 3/2011 Chong et al.
2011/0124996 A1 5/2011 Reinke et al.
2011/0144586 A1 6/2011 Michaud et al.
2011/0160652 A1 6/2011 Yodfat et al.
2011/0178472 A1 7/2011 Cabiri
2011/0190694 A1 8/2011 Lanier, Jr. et al.
2011/0202005 A1 8/2011 Yodfat et al.
2011/0218495 A1 9/2011 Remde
2011/0230833 A1 9/2011 Landman et al.
2011/0251509 A1 10/2011 Beyhan et al.
2011/0313680 A1* 12/2011 Doyle, III .............. G16H 20/60
702/19
2011/0316562 A1 12/2011 Cefai et al.
2012/0003935 A1 1/2012 Lydon et al.
2012/0010594 A1 1/2012 Holt et al.
2012/0030393 A1 2/2012 Ganesh et al.
2012/0053556 A1 3/2012 Lee
2012/0078067 A1 3/2012 Kovatchev et al.
2012/0078161 A1 3/2012 Masterson et al.
2012/0078181 A1 3/2012 Smith et al.
2012/0101451 A1 4/2012 Boit et al.
2012/0123234 A1 5/2012 Atlas et al.
2012/0136336 A1 5/2012 Mastrototaro et al.
2012/0190955 A1 7/2012 Rao et al.
2012/0203085 A1 8/2012 Rebec
2012/0203178 A1 8/2012 Tverskoy
2012/0215087 A1 8/2012 Cobelli et al.
2012/0225134 A1 9/2012 Komorowski
2012/0226259 A1 9/2012 Yodfat et al.
2012/0232520 A1 9/2012 Sloan et al.
2012/0238851 A1 9/2012 Kamen et al.
2012/0271655 A1 10/2012 Knobel et al.
2012/0277668 A1 11/2012 Chawla et al.
2012/0282111 A1 11/2012 Nip et al.
2012/0295550 A1 11/2012 Wilson et al.
2013/0030358 A1 1/2013 Yodfat et al.
2013/0144137 A1* 6/2013 Zalevsky ............. A61B 5/0066
600/314
2013/0158503 A1 6/2013 Kanderian, Jr. et al.
2013/0178791 A1 7/2013 Javitt
2013/0231642 A1 9/2013 Doyle et al.
2013/0253472 A1 9/2013 Cabiri
2013/0261406 A1 10/2013 Rebec et al.
2013/0296823 A1 11/2013 Melker et al.
2013/0317753 A1 11/2013 Kamen et al.
2013/0338576 A1 12/2013 OConnor et al.
2014/0005633 A1 1/2014 Finan
2014/0074033 A1 3/2014 Sonderegger et al.
2014/0121635 A1 5/2014 Hayter
2014/0128839 A1 5/2014 Dilanni et al.
2014/0135880 A1 5/2014 Baumgartner et al.
2014/0146202 A1 5/2014 Boss et al.
2014/0180203 A1 6/2014 Budiman et al.
2014/0180240 A1 6/2014 Finan et al.
2014/0200426 A1 7/2014 Taub et al.
2014/0200559 A1 7/2014 Doyle et al.
2014/0230021 A1 8/2014 Birthwhistle et al.
2014/0276554 A1* 9/2014 Finan ................ A61M 5/14244
604/504
2014/0276556 A1 9/2014 Saint et al.
2014/0278123 A1 9/2014 Prodhom et al.
2014/0309615 A1 10/2014 Mazlish
2014/0316379 A1 10/2014 Sonderegger et al.
2014/0325065 A1 10/2014 Birtwhistle et al.
2015/0018633 A1 1/2015 Kovachev et al.
2015/0025329 A1 1/2015 Amarasingham et al.
2015/0025495 A1 1/2015 Peyser
2015/0120317 A1 4/2015 Mayou et al.
2015/0134265 A1 5/2015 Kohlbrecher et al.
2015/0165119 A1 6/2015 Palerm et al.
2015/0173674 A1 6/2015 Hayes et al.
2015/0213217 A1 7/2015 Amarasingham et al.
2015/0217052 A1 8/2015 Keenan et al.
2015/0217053 A1 8/2015 Booth et al.
2015/0265767 A1 9/2015 Vazquez et al.
2015/0306314 A1 10/2015 Doyle et al.
2015/0351671 A1 12/2015 Vanslyke et al.
2015/0366945 A1 12/2015 Greene
2016/0015891 A1 1/2016 Papiorek
2016/0038673 A1 2/2016 Morales
2016/0038689 A1 2/2016 Lee et al.
2016/0051749 A1 2/2016 Istoc
2016/0082187 A1 3/2016 Schaible et al.
2016/0089494 A1 3/2016 Guerrini
2016/0175520 A1 6/2016 Palerm et al.
2016/0228641 A1 8/2016 Gescheit et al.
2016/0243318 A1 8/2016 Despa et al.
2016/0256087 A1 9/2016 Doyle et al.
2016/0287512 A1 10/2016 Cooper et al.
2016/0302054 A1 10/2016 Kimura et al.
2016/0331310 A1 11/2016 Kovatchev
2016/0354543 A1 12/2016 Cinar et al.
2017/0049386 A1 2/2017 Abraham et al.
2017/0143899 A1 5/2017 Gondhalekar et al.
2017/0143900 A1 5/2017 Rioux et al.
2017/0156682 A1 6/2017 Doyle et al.
2017/0173261 A1 6/2017 OConnor et al.
2017/0189625 A1 7/2017 Cirillo et al.
2017/0224920 A1* 8/2017 Finan ................ A61M 5/14244
2017/0249445 A1* 8/2017 Devries .................. A61B 5/145
2017/0281877 A1 10/2017 Marlin et al.
2017/0296746 A1 10/2017 Chen et al.
2017/0311903 A1 11/2017 Davis et al.
2017/0348482 A1 12/2017 Duke et al.
2018/0036495 A1 2/2018 Searle et al.
2018/0040255 A1 2/2018 Freeman et al.
2018/0075200 A1 3/2018 Davis et al.
2018/0075201 A1 3/2018 Davis et al.
2018/0075202 A1 3/2018 Davis et al.
2018/0092576 A1 4/2018 Ambrosio et al.
2018/0126073 A1 5/2018 Wu et al.
2018/0169334 A1 6/2018 Grosman et al.
2018/0200434 A1 7/2018 Mazlish et al.
2018/0200438 A1 7/2018 Mazlish et al.
2018/0200441 A1 7/2018 Desborough et al.
2018/0204636 A1 7/2018 Edwards et al.
2018/0277253 A1 9/2018 Gondhalekar et al.
2018/0289891 A1 10/2018 Finan et al.
2018/0342317 A1 11/2018 Skirble et al.
2018/0369479 A1 12/2018 Hayter et al.
2019/0076600 A1 3/2019 Grosman et al.
2019/0159705 A1* 5/2019 Sim .................... A61B 5/14532
2019/0240403 A1 8/2019 Palerm et al.
2019/0336683 A1 11/2019 O'Connor et al.
2019/0336684 A1 11/2019 O'Connor et al.
2019/0348157 A1 11/2019 Booth et al.
2020/0046268 A1 2/2020 Patek et al.
2020/0101222 A1 4/2020 Lintereur et al.
2020/0101223 A1 4/2020 Lintereur et al.
2020/0101225 A1 4/2020 O'Connor et al.
2020/0219625 A1 7/2020 Kahlbaugh
2020/0342974 A1 10/2020 Chen et al.

(56) References Cited

U.S. PATENT DOCUMENTS

| | | | |
|---|---|---|---|
| 2021/0050085 | A1 | 2/2021 | Hayter et al. |
| 2021/0098105 | A1 | 4/2021 | Lee et al. |
| 2022/0023536 | A1 | 1/2022 | Graham et al. |

FOREIGN PATENT DOCUMENTS

| | | | | | |
|---|---|---|---|---|---|
| CN | 1297140 | A | | 5/2001 | |
| DE | 19756872 | A1 | | 7/1999 | |
| EP | 0341049 | A2 | | 11/1989 | |
| EP | 0496305 | A2 | | 7/1992 | |
| EP | 0549341 | A1 | | 6/1993 | |
| EP | 1491144 | A1 | | 12/2004 | |
| EP | 0801578 | B1 | | 7/2006 | |
| EP | 2666520 | A1 | | 10/2009 | |
| EP | 2139382 | A1 | | 1/2010 | |
| EP | 2397181 | A1 | | 12/2011 | |
| EP | 2695573 | A2 | | 2/2014 | |
| EP | 2830499 | A1 | | 2/2015 | |
| EP | 2943149 | A1 | | 11/2015 | |
| EP | 3177344 | A1 | | 6/2017 | |
| EP | 3314548 | A1 | | 5/2018 | |
| EP | 2897071 | B1 | | 5/2019 | |
| EP | 3607985 | A1 | | 2/2020 | |
| GB | 2443261 | A | | 4/2008 | |
| JP | 51125993 | A | | 11/1976 | |
| JP | 02131777 | A | | 5/1990 | |
| JP | 2004283378 | A | | 10/2007 | |
| JP | 2017525451 | A | | 9/2017 | |
| JP | 2019525276 | A | | 9/2019 | |
| TW | 200740148 | A | | 10/2007 | |
| TW | M452390 | U | | 5/2013 | |
| WO | 9800193 | A1 | | 1/1998 | |
| WO | 9956803 | A1 | | 11/1999 | |
| WO | 0030705 | A1 | | 6/2000 | |
| WO | 0032258 | A1 | | 6/2000 | |
| WO | 0172354 | A2 | | 10/2001 | |
| WO | 2002015954 | A1 | | 2/2002 | |
| WO | 0243866 | A2 | | 6/2002 | |
| WO | 02082990 | A1 | | 10/2002 | |
| WO | 03016882 | A1 | | 2/2003 | |
| WO | 03039362 | A1 | | 5/2003 | |
| WO | 03045233 | A1 | | 6/2003 | |
| WO | 2004043250 | A1 | | 5/2004 | |
| WO | 04092715 | A1 | | 10/2004 | |
| WO | 2005051170 | A2 | | 6/2005 | |
| WO | WO-2005057175 | A2 | * | 6/2005 | ............. A61B 5/145 |
| WO | 2005082436 | A1 | | 9/2005 | |
| WO | 05110601 | A1 | | 11/2005 | |
| WO | WO-2005113036 | A1 | * | 12/2005 | ............. A61B 5/411 |
| WO | 2006053007 | A2 | | 5/2006 | |
| WO | 2007064835 | A2 | | 6/2007 | |
| WO | 2007078937 | A1 | | 7/2007 | |
| WO | 2008024810 | A2 | | 2/2008 | |
| WO | 2008029403 | A1 | | 3/2008 | |
| WO | 2008133702 | A1 | | 11/2008 | |
| WO | 2009045462 | A1 | | 4/2009 | |
| WO | 2009049252 | A1 | | 4/2009 | |
| WO | 2009066287 | A3 | | 5/2009 | |
| WO | 2009066288 | A1 | | 5/2009 | |
| WO | 2009098648 | A2 | | 8/2009 | |
| WO | 2009134380 | A2 | | 11/2009 | |
| WO | 2010053702 | A1 | | 5/2010 | |
| WO | 2010132077 | A1 | | 11/2010 | |
| WO | 2010138848 | A1 | | 12/2010 | |
| WO | 2010147659 | A2 | | 12/2010 | |
| WO | 2011095483 | A1 | | 8/2011 | |
| WO | 2012045667 | A2 | | 4/2012 | |
| WO | 2012108959 | A1 | | 8/2012 | |
| WO | 2012134588 | A1 | | 10/2012 | |
| WO | 2012178134 | A2 | | 12/2012 | |
| WO | WO-2012177353 | A1 | * | 12/2012 | ......... A61B 5/14532 |
| WO | 2013078200 | A1 | | 5/2013 | |
| WO | 2013134486 | A2 | | 9/2013 | |
| WO | 20130149186 | A1 | | 10/2013 | |
| WO | 2013177565 | A1 | | 11/2013 | |
| WO | 2013182321 | A1 | | 12/2013 | |
| WO | 2014109898 | A1 | | 7/2014 | |
| WO | 2014110538 | A1 | | 7/2014 | |
| WO | 2014194183 | A2 | | 12/2014 | |
| WO | 2015056259 | A1 | | 4/2015 | |
| WO | 2015061493 | A1 | | 4/2015 | |
| WO | WO-2015073211 | A1 | * | 5/2015 | ......... A61B 5/14532 |
| WO | 2015081337 | A2 | | 6/2015 | |
| WO | 2015187366 | A1 | | 12/2015 | |
| WO | 2016004088 | A1 | | 1/2016 | |
| WO | 2016022650 | A1 | | 2/2016 | |
| WO | 2016041873 | A1 | | 3/2016 | |
| WO | 2016089702 | A1 | | 6/2016 | |
| WO | 2016141082 | A1 | | 9/2016 | |
| WO | 2017004278 | A1 | | 1/2017 | |
| WO | 2017091624 | A1 | | 6/2017 | |
| WO | 2017105600 | A1 | | 6/2017 | |
| WO | 2017184988 | A1 | | 10/2017 | |
| WO | 2017205816 | A1 | | 11/2017 | |
| WO | 2018009614 | A1 | | 1/2018 | |
| WO | 2018067748 | A1 | | 4/2018 | |
| WO | 2018120104 | A1 | | 7/2018 | |
| WO | 2018136799 | A1 | | 7/2018 | |
| WO | 2018204568 | A1 | | 11/2018 | |
| WO | 2019077482 | A1 | | 4/2019 | |
| WO | 2019094440 | A1 | | 5/2019 | |
| WO | 2019213493 | A1 | | 11/2019 | |
| WO | 2019246381 | A1 | | 12/2019 | |
| WO | WO-2019246217 | A1 | * | 12/2019 | |
| WO | 2020081393 | A1 | | 4/2020 | |
| WO | 2021011738 | A1 | | 1/2021 | |

OTHER PUBLICATIONS

Anonymous: “Artificial pancreas—Wikipedia”, Mar. 13, 2018 (Mar. 13, 2018), XP055603712, Retrieved from the Internet: URL: https://en.wikipedia.org/wiki/Artificial_pancreas [retrieved on Jul. 9, 2019] section “Medical Equipment” and the figure labeled “The medical equipment approach to an artifical pancreas”.

Kaveh et al., “Blood Glucose Regulation via Double Loop Higher Order Sliding Mode Control and Multiple Sampling Rate.” Paper presented at the proceedings of the 17th IFAC World Congress, Seoul, Korea (Jul. 2008).

Dassau et al., “Real-Time Hypoglycemia Prediction Suite Using Contineous Glucose Monitoring,” Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., “Control-Relevant Models for Glucose Control using A Priori Patient Characteristics”, IEEE Transactions on Biomedical Engineering, vol. 59, No. 7, (Jul. 1, 2012) pp. 1839-1849.

Doyle III et al., “Run-to-Run Control Strategy for Diabetes Management.” Paper presented at 23rd Annual International Conference of the IEEE Engineering in Medicine and Biology Society, Istanbul, Turkey. (Oct. 2001).

Bequette, B.W., and Desemone, J., “Intelligent Dosing Systems”: Need for Design and Analysis Based on Control Theory, Diabetes Technology and Therapeutics 9(6): 868-873 (2004).

Parker et al., “A Model-Based Agorithm for Blood Gucose Control in Type 1 Diabetic Patients.” IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

“How to Create a QR Code that Deep Links to Your Mobile App”, Pure Oxygen Labs, web<https://pureoxygenlabs.com/how-to-create-a-qr-codes-that-deep-link-to-your-mobile-app/> Year:2017.

(56) References Cited

OTHER PUBLICATIONS

"Read NFC Tags with an iPHone App on IOS 11", GoToTags, 11 Sep. 2017, web <https://gototags.com/blog/read-nfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 pages.
International Search Report and Written Opinion for the International Patent Application No. PCT/US2021/022694, mailed Jun. 25, 2021, 13 pages.
Kohdaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Anonymous: "Fuzzy control system", Wikipedia, Jan. 10, 2020. URL: https://en.wikipedia.org/w/index.php?title=Fuzzy_control_system&oldid=935091190.
International Search Report and Written Opinion for the International Patent Application No. PCT/US2021/016283, mailed Jun. 2, 2021, 15 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
Unger, Jeff, et al., "Glucose Control in the Hospitalized Patient," Emerg. Med 36(9):12-18 (2004).
Glucommander FAQ downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Searching Authority, Invitation to Pay Additional Fees, International Application No. PCT/US2006/004929, mailed Jul. 27, 2006.
Farkas et al. ""Single-Versus Triple-Lumen Central Catheter-Related Sepsis: A Prospective Randomized Study in a Critically Ill Population"" The American Journal of Medicine September 1992vol. 93 p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
Gorke, A. "Microbial contamination of haemodialysis catheter connections." EDTNA/ERCA journal (English ed.) vol. 31,2 (2005): 79-84. doi:10.1111/j.1755-6686.2005.tb00399.x.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Templeton et al., "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010.
International Search Report and Written Opinion in PCT/US2008/079641 dated Feb. 25, 2009.
Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73,1998.
Berger, "An Enhanced Algorithm for Linear Multivariate Calibration," Analytical Chemistry, vol. 70, No. 3, pp. 623-627, Feb. 1, 1998.
Billman et. al.,"Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.
International Preliminary Report on Patentability for the International Patent Application No. PCT/US2019/053603, mailed Apr. 8, 2021, 9 pages.

(56) References Cited

OTHER PUBLICATIONS

International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,Vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).
International Search Report and Written Opinion for the InternationalPatent Application No. PCT/US2021/018297, mailed May 18, 2021, 18 pages.
An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.
International Search Report and Written Opinion for the International Patent Application No. PCT/US2021/017441, mailed May 25, 2021, 12 pages.
International Search Report and Written Opinion for the InternationalPatent Application No. PCT/US2021/017664, mailed May 26, 2021, 16 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
European Search Report for the European Patent Application No. 21168591.2, mailed Oct. 13, 2021, 04 pages.
International Search Report and Written Opinion for the International Patent Application No. PCT/US2021/041954, mailed Oct. 25, 2021, 13 pages.
International Search Report and Written Opinion for the International Patent Application No. PCT/US2021/047771, mailed Dec. 22, 2021, 11 pages.
International Search Report and Written Opinion for the International Patent Application No. PCT/US2021/052855, mailed Dec. 22, 2021, 11 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial beriod in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

(56) References Cited

OTHER PUBLICATIONS

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2022/012896, mailed Apr. 22, 2022, 15 pages.

* cited by examiner

TECHNIQUES FOR IMAGE-BASED MONITORING OF BLOOD GLUCOSE STATUS

FIELD OF THE INVENTION

The present disclosure generally relates to automated insulin monitoring processes, and, more particularly, to processes for determining an insulin condition of a patient, such as a hypoglycemic state, using image-based insulin and/or blood glucose information.

BACKGROUND

Diabetes mellitus is a serious medical condition caused by an inability to adequately control blood glucose levels. Typical treatments involve injecting affected individuals with the hormone insulin in an attempt to maintain blood glucose values within a desired, healthy range. Type 1 diabetes mellitus (T1D) results from an autoimmune response in which the immune system attacks pancreatic beta cells so that they no longer produce insulin. For type 2 diabetes mellitus (T2D), the pancreas may produce insulin, but it is either not a sufficient amount and/or the body's cells do not adequately respond to the insulin.

Patient responses to insulin may often be unpredictable due to the complicated and dynamic nature of the human body's response to insulin. As a result, it is not uncommon for patients to end up in a hypoglycemic (blood sugar levels below normal) or hyperglycemic (blood sugar levels above normal) state even while undergoing insulin treatment therapy. Such conditions may be harmful for many reasons. For example, hypoglycemia may create an immediate risk of a severe medical event (for instance, seizures, coma, cognitive dysfunction), while hyperglycemia creates long term negative health effects as well as the risk of ketoacidosis (ketones in the blood).

To prevent harmful conditions, patients typically use conventional monitoring techniques, including self-monitoring of blood glucose (SMBG) (for example, through a manual fingerstick-based technique) or continuous glucose monitoring (CGM) (for example, through sensors attached to the body of the patient). However, conventional monitoring techniques are not able to fully capture or process information influencing patient blood glucose conditions. In addition, SMBG and/or CGM monitoring may not always be feasible and control mechanisms may not be best suited for given external conditions and/or lifestyle activities.

Accordingly, it would be beneficial and advantageous to have a system, a device and/or a technique for effectively and accurately monitoring blood glucose conditions of diabetic patients.

Figure 1:
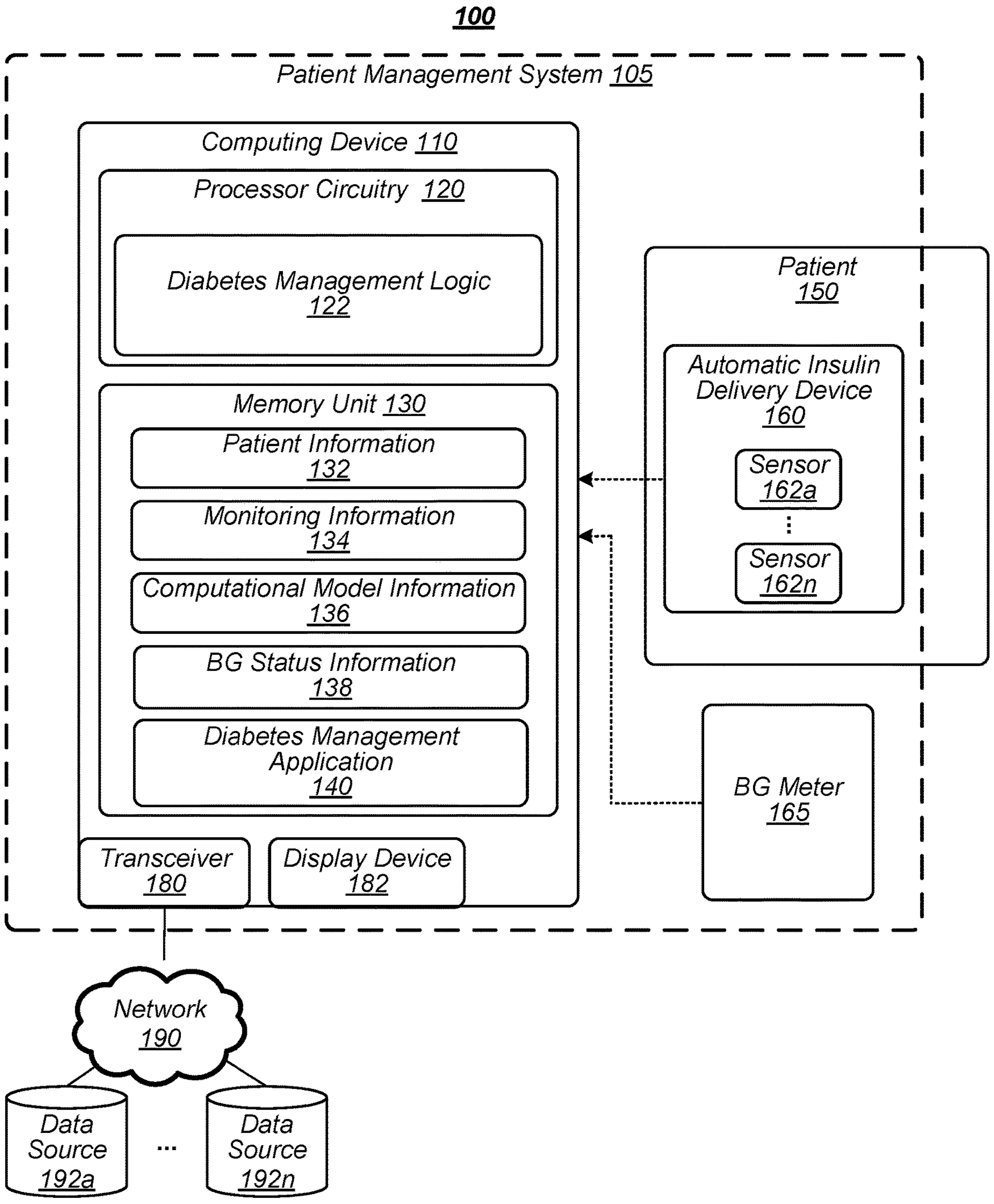
FIG. 1 illustrates a first exemplary operating environment in accordance with the present disclosure.

The drawings are not necessarily to scale. The drawings are merely representations, not intended to portray specific parameters of the disclosure. The drawings are intended to depict example embodiments of the disclosure, and therefore should not be considered as limiting in scope. In the drawings, like numbering represents like elements

DETAILED DESCRIPTION

The described technology generally relates to a blood glucose (BG) monitoring process for monitoring the BG status of a patient undergoing diabetes treatment therapy. In various embodiments, the BG status of a patient may include a prediction of an imminent state (or a confidence level of the occurrence of an imminent state), such as a hypoglycemic state and/or a hyperglycemic state. In some embodiments, monitoring information associated with a patient may be obtained and processed to generate a monitoring information structure. Non-limiting examples of monitored information may include patient physiological information (for instance, heart rate, temperature, and/or the like), activity information, meal information, BG information (for instance, BG levels, insulin-on-board (IOB) information), insulin infusion information, and/or the like. An illustrative and non-restrictive example of a monitoring information structure may include a graph, for instance, of a plurality of monitored information data streams. The BG monitoring process may transform the monitoring information structure into a monitoring image, such as a digital image or electronic image file. The monitoring image may be processed via a computational model trained to determine a BG status based on image information. The output of the computational model may provide a BG status including, without limitation, an indication of whether the patient is in or is heading into a hypoglycemic state or a hyperglycemic state. In various embodiments, the BG monitoring process may administer or cause the administration of insulin to patient (including reducing or eliminating a current or upcoming insulin infusion) and/or provide BG status information to patient based on the determined BG status (for example, a message that a hypoglycemic state is imminent).

In people with diabetes, hypoglycemia (BG levels below normal) is a result of relative or absolute excess in insulin levels and compromised physiological defenses against failing plasma glucose concentrations. Alternatively, hyperglycemia (BG levels above normal) can result from insufficient bolus infusions, inadequate basal rates, and/or combinations of additional factors such as food intake, insufficient exercise, drug use, and/or the like. Consequences of hypoglycemia may include seizures, coma, cognitive dysfunction, and may even result in death. The physiological responses to trending low glucose concentrations include secretion of glucagon, epinephrine, growth hormone, and finally cortisol.

Hypoglycemia may be classified in various levels, including, for example level 1 (≤70 mg/dL), level 2 (<54 mg/dL), and level3 (no specific threshold). Level 3 is generally considered severe level which is associated with extreme cognitive impairment that may require external assistance for recovery. Accordingly, BG monitoring for diabetic patients is vital to patient health and well-being.

Advancements in technologies have allowed patients to use SMBG (self-monitoring of blood glucose) or CGM (continuous glucose monitors) to have more insights into blood glucose levels and other physiological information. Instances of hypoglycemia or hyperglycemia may be able to be reduced or even avoided if patients and/or diabetes management systems were able to fully take advantage of monitored influencers. However, conventional monitoring technology is not able to effectively and accurately use monitoring information to generate meaningful monitoring decisions and/or treatments (for instance, insulin infusion control). In addition, monitoring is not always feasible and as a control mechanism may not be best suited for external conditions and lifestyle activities of many patients.

In addition, conventional monitoring mechanisms for prediction typically involve algorithms such as linear regression or combination of regression and other algorithms to predict imminent hypoglycemia or other health conditions. For example, one standard technique attempts to predict imminent hypoglycemia by graphing CGM values, basal and/or bolus insulin deliveries, and IOB and using the slope of the CGM to calculate a prediction. This algorithm, however, is influenced by real-time glucose values and does not factor in patterns observed in the individualized physiological response from historical perspective. Accordingly, such conventional approaches lack the ability to provide accurate, personalized solutions required to effectively treat diabetic patients and, in particular, predict hypoglycemic and/or hyperglycemic events.

Accordingly, some embodiments may use computational models to process image information of monitored information to accurately predict BG conditions, such as an imminent hypoglycemic event. A non-limiting example of a computational model may be or may include a neural network (NN), for instance, a convoluted neural network (CNN). In some embodiments, for example, a CNN-based approach may increase prediction accuracy by using a model which is built from historical data for all the instances of true hypoglycemia which can predict the future occurrence in the form of probability. In exemplary embodiments, the CNN model may be based on using CGM curves (along with other information, such as insulin dosages, IOB, and/or the like) as images fed through the CNN for positive outcomes of the hypoglycemia. For example, as described in more detail in the present disclosure, CGM graph regions indicating true and false hypoglycemia events may be extracted in the form of images and provided to the computational model for training. Once the model is trained, a combination of regression model and image model can be used for better prediction.

Although a NN and, in particular, a CNN is used as an example computational model in the present disclosure, embodiments are not so limited, as a computational model may include any existing or future developed computational model capable of operating according to some embodiments. Non-limiting examples of computational models may include an artificial intelligence (AI) model, an artificial neural network (ANN), a deep learning (DL) network, a deep neural network (DNN), a recurrent neural network (RNN), and/or the like.

Therefore, BG monitoring processes according to some embodiments may provide multiple technological advantages and technical features over conventional systems, including improvements to computing technology. One non-limiting example of a technological advantage may include providing a computing device capable of predicting a BG condition, such as imminent hypoglycemia, based on image information. Another non-limiting example of a technological advantage may include a BG monitoring process capable of more accurately predicting BG conditions than capable using conventional techniques. A further non-limiting example of a technological advantage may include controlling automatic insulin infusion processes and devices based on BG condition prediction information (for instance, stopping or reducing a scheduled insulin injection based on a predicted hypoglycemic event, increasing a volume of injected insulin based on a predicted hyperglycemic event, and/or the like). An additional example of a technological advantage may include providing an accurate and effective warning or messaging process to alert patients to imminent negative BG conditions. Another example of a technological advantage may include providing a process for providing image signal-based processing of BG information, for example, using computational models, such as a CNN, to make predictions of BG conditions based on image information (as opposed to directly analyzing the values of monitored information, such as a linear analysis).

In addition, some embodiments may provide one or more practical applications of BG monitoring processes, algorithms, and/or the like described in the present disclosure. Illustrative and non-limiting practical applications may include treating diabetes based on predictions generated using BG monitoring processes operating according to some embodiments, reducing or even preventing the occurrence of negative BG events, such as hypoglycemia, due to the counteractive and/or messaging capabilities of BG monitoring processes according to some embodiments, providing accurate BG condition information that is not capable of being generated using conventional techniques. Other technological advantages, improvements, and/or practical applications are provided by embodiments described in the present disclosure and would be understood by persons of skill in the art. Embodiments are not limited in this context.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In this Detailed Description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include a patient management system 105. In various embodiments, patient management system 105 may include a computing device 110 that, in some embodiments, may be communicatively coupled to network 190 via a transceiver 180. Computing device 110 may be or may include one or more logic devices, including, without limitation, a server computer, a client computing device, a personal computer (PC), a workstation, a laptop, a notebook computer, a smart phone, a tablet computing device, a personal diabetes management (PDM) device, and/or the like. Embodiments are not limited in this context.

Patient management system 105 may include or may be communicatively coupled to an automatic insulin delivery (AID) device 160 configured to deliver insulin (and/or other medication) to patient 150. AID device 160 may be a wearable device. For example, AID device 160 may be directly coupled to patient 150 (for instance, directly attached to a body part and/or skin of the user via an adhesive and/or other attachment component).

AID device 160 may include a number of components to facilitate automated delivery of insulin to patient 150. For example, AID device 160 may include a reservoir for storing insulin, a needle or cannula for delivering insulin into the body of the person, and a pump for transferring insulin from the reservoir, through the needle or cannula, and into the body of patient. AID device 160 may also include a power source, such as a battery, for supplying power to the pump and/or other components of automatic insulin delivery device 160. Embodiments are not limited in this context, for example, as AID device 160 may include more or fewer components.

AID device 160 may store and provide any medication or drug to the user. In various embodiments, AID device 160 may be or may include a wearable AID device. For example, AID device 160 may be the same or similar to an OmniPod® device or system provided by Insulet Corporation of Acton, Massachusetts, United States, for example, as described in U.S. Pat. Nos. 7,303,549; 7, 137,964; and/or 6,740,059, each of which is incorporated herein by reference in its entirety.

In some embodiments, computing device 110 may be a smart phone, PDM, or other mobile computing form factor in wired or wireless communication with automatic insulin delivery device 160. For example, computing device 110 and AID device 160 may communicate via various wireless protocols, including, without limitation, Wi-Fi (i.e., IEEE 802.11), radio frequency (RF), Bluetooth™, Zigbee™, near field communication (NFC), Medical Implantable Communications Service (MICS), and/or the like. In another example, computing device 110 and adjustment compliance device may communicate via various wired protocols, including, without limitation, universal serial bus (USB), Lightning, serial, and/or the like. Although computing device 110 (and components thereof) and AID device 160 are depicted as separate devices, embodiments are not so limited. For example, in some embodiments, computing device 110 and AID device 160 may be a single device. In another example, some or all of the components of computing device 110 may be included in automatic insulin delivery device 160. For example, AID device 160 may include processor circuitry 120, memory unit 130, and/or the like. In some embodiments, each of computing device 110 and AID device 160 may include a separate processor circuitry 120, memory unit 130, and/or the like capable of facilitating BG monitoring processes according to some embodiments, either individually or in operative combination. Embodiments are not limited in this context (see, for example, FIG. 2).

AID device 160 may include or may be communicatively coupled to one or more sensors 162*a-n* operative to detect, measure, or otherwise determine various physiological characteristics of patient 150. For example, a sensor 162*a-n* may be or may include a CGM sensor operative to determine blood glucose measurement values of patient 150. In another example, a sensor 162*a-n* may include a heart rate sensor, temperature sensor, and/or the like.

In some embodiments, patient management system 105 may include a BG meter 165, for example, for manually measuring BG of patient 150 via a manual, fingerstick process. A non-limiting example of a BG meter may include a FreeStyle BG meter produced by Abbot Laboratories of Abbot Park, Illinois, United States. Embodiments are not limited in this context.

Computing device 110 (and/or automatic insulin delivery device 160) may include a processor circuitry 120 that may include and/or may access various logics for performing processes according to some embodiments. For instance, processor circuitry 120 may include and/or may access a diabetes management logic 122. Processing circuitry 120, diabetes management logic 122, and/or portions thereof may be implemented in hardware, software, or a combination thereof. The functions, processes, algorithms, and/or the like (for example, a BG monitoring process and/or an insulin infusion process (for instance, an AP or AID algorithm of AID device 160) described according to some embodiments may be performed by processor circuitry and/or diabetes management logic 122 (for example, via executing diabetes management application 140) by computing device 110, automatic insulin delivery device 160, and/or a combination thereof.

Processing circuitry 120, memory unit 130, and associated components are depicted within computing device 110 to simplify FIG. 1 (for instance, all or a portion of processing circuitry 120, memory unit 130, and/or associated components may be arranged within automatic insulin delivery device 160). Accordingly, embodiments of functionality, processes (for instance, a BG monitoring process and/or an insulin infusion process), and/or the like described in the present disclosure with respect to computing device 110 and/or components thereof may be performed in whole or in part by automatic insulin delivery device 160.

As used in this application, the terms "logic," "component," "layer," "system," "circuitry," "decoder," "encoder," "control loop," and/or "module" are intended to refer to a computer-related entity, either hardware, a combination of hardware and software, software, or software in execution. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a computational model or application, a computational model, a CNN model, an AI model or application, an ML model or application, a proportional-integral-derivative (PID) controller, FG circuitry, variations thereof, combinations of any of the foregoing, and/or the like.

Although diabetes management logic 122 is depicted in FIG. 1 as being within processor circuitry 120, embodiments are not so limited. For example, diabetes management logic 122 and/or any component thereof may be located within an accelerator, a processor core, an interface, an individual processor die, implemented entirely as a software application (for instance, a diabetes management application 140) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD)) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store various types of information and/or applications for a BG monitoring process according to some embodiments. For example, memory unit 130 may store patient information 132, monitoring information 134, computational model information 136, BG status information 138, and/or diabetes management application 140. In some embodiments, patient information 132, monitoring information 134, computational model information 136, BG status information 138, and/or diabetes management application 140, and/or portions thereof may be stored in one or more data stores 192*a-n* accessible to computing device 110 (and/or automatic insulin delivery device 160) via network 190. For example, data stores 192*a-n* may include electronic health records, cloud-based data or services, and/or the like.

In some embodiments, diabetes management application 140 may be or may include an application being executed on computing device 110 and/or AID device 160 (including a mobile application, "mobile app," or "app" executing on a mobile device form factor). For example, in various embodiments, diabetes management application 140 may be or may include an application the same or similar to the Omnipod® Mobile App, Glooko, Omnipod® DASH™ PDM software, and/or the like provided by Insulet Corporation of Acton, Massachusetts, United States. In addition or in the alternative, diabetes management application 140 may be or may include an application operative to control components of automatic insulin delivery device (for instance, a pump, sensors 162*a-n,* and/or the like) to infuse patient 150 with insulin, such as an AID application. For example, diabetes management application 140 may be or may include an AID application to monitor patient blood glucose values, determine an appropriate level of insulin based on the monitored glucose values (e.g., blood glucose concentrations and/or blood glucose measurement values) and other information, such as user-provided information, including, for example, carbohydrate intake, exercise times, meal times, and/or the like, and perform an insulin infusion process according to some embodiments to maintain a user's blood glucose value within an appropriate range. In some embodiments, diabetes management application 140 may operate to present information to patient 150 or caregiver of patient 150 via display device 182. For example, diabetes management application 140 may display a BG condition, such as an alert of an imminent hypoglycemic condition on display device 182.

In various embodiments, patient information 132 may include information associated with patient 150, including, without limitation, demographic information, physical information (for instance, height, weight, and/or the like), diabetes condition information (for instance, type of diagnosed diabetes (T1D or T2D)), insulin needs (for instance, MDI information, TDI information, insulin types, basal dosage information, bolus dosage information, and/or the like), activity information (for instance, meals and/or meal times, carbohydrate intake, exercise information, and/or the like), insulin sensitivity information, IOB information, BG events (for example, hypoglycemic episodes or hyperglycemic episodes), and/or the like. In some embodiments, at least a portion of patient information 132 may be manually entered by patient 150 or a caregiver, for example, via a user interface of diabetes management application 140. In some embodiments, patient information 132 may include historical information, such as historical values associated with mealtimes, carbohydrate intake, exercise times, and/or the like.

In some embodiments, monitoring information 134 may include information determined via sensors 162*a-n* and/or BG meter 165. For example, monitoring information 134 may include CGM information and/or manual BG measurement information (for instance, BG concentrations or other BG measurement values), temperature information, heart rate information, and/or the like. In exemplary embodiments, monitoring information 134 may include historical information, for instance, historical BG values of patient 150. In some embodiments, monitoring information 134 may include real-time or substantially real-time information. Accordingly, BG monitoring processes according to some embodiments may operate to determine BG status information 138 (such as predictions) based on real-time or substantially real-time information.

In exemplary embodiments, computational model information 136 may include information associated with computational models used in BG monitoring processes according to some embodiments. Non-limiting examples of computational models may include a NN, a CNN, an AI model, an ML model, an ANN, a DL network, a DNN, an RNN, and any other computational model now known or developed in the future capable of operating with some embodiments. In various embodiments, a computational model may be or may include a CNN. In some embodiments, computational model information 136 may include training data for training computational models. In various embodiments, the training data may include training data from historical information of patient 150 (for instance, historical BG information, historical hypoglycemic episodes, and/or the like). In exemplary embodiments, the training data may include training data from a population of individuals (for instance, with the same or similar characteristics as patient 150) that do not include patient 150. In this manner, computational models may be trained using a large volume of historical training data.

In general, a neural network may include multiple layers of interconnected neurons that can exchange data between one another. The layers include an input layer for receiving input data, a hidden layer, and an output layer for providing a result. The hidden layer is referred to as hidden because it may not be directly observable or have its input directly accessible during the normal functioning of the neural network. In some implementations, the neurons and connections between the neurons can have numeric weights, which can be tuned during training. For example, training data can be provided to the input layer of the neural network, and the neural network can use the training data to tune one or more numeric weights of the neural network.

In some examples, the neural network can be trained using backpropagation. Backpropagation can include determining a gradient of a particular numeric weight based on a difference between an actual output of the neural network and a desired output of the neural network. Based on the gradient, one or more numeric weights of the neural network can be updated to reduce the difference, thereby increasing the accuracy of the neural network. This process can be repeated multiple times to train the neural network. For example, this process can be repeated hundreds or thousands of times to train the neural network. In some examples, the neural network is a feed-forward (or forward propagating) neural network. In a feed-forward neural network, every neuron only propagates an output value to a subsequent layer of the neural network. For example, data may only move one direction (forward) from one neuron to the next neuron in a feed-forward neural network.

In some embodiments, the neural network may be a CNN (see, for example, FIG. 8) configured to analyze visual images. In general, a CNN may include an input layer, multiple hidden layers, and an output layer configured to implement a feature learning function and a classification function. The hidden layers (or feature learning layers) may include one or more of a convolution layer, rectified Linear Unit (a ReLU layer or an activation layer), and a pooling layer. In the classification function, there is a fully connected layer, which flattens out the output from previous layers into a vector. The fully connected layer is designed to harness the learning that has been done in the previous layers. Finally, a SoftMax function is applied to the fully connected layer, resulting in a set of probability values, indicating the probability that the input image is one of a specific class of outputs.

The pooling layer generally shrinks an input image stack. Max pooling, for example, takes the maximum of its neighbors, while average pooling takes the average of its neighbors. Pooling reduces the size of the activations that are fed to the next layer, which reduces the memory footprint and improves the overall computational efficiency. The ReLU layer changes negative values to zero. The ReLU layer acts as an activation function, ensuring non-linearity as the image data moves through each layer in the network. In one example, pooling layers may run kernels on each cluster of an image to form a combined representation for that cluster. This combined representation is then passed to the next layer. The cluster which maps the criteria of the filter being applied will have more representation in weight.

CNNs may be generally defined as multiples of these different layers, and the layers are often repeated. Each time, as the image goes through convolution layers, it gets more filtered, and it gets smaller as it goes through pooling layers. In the fully connected layer, a list of feature values becomes a list of votes. Fully connected layers can also be stacked together.

Each layer of the CNN contains neurons. Unlike regular neural networks, a CNN neuron is not connected to every other neuron in the previous layer, but only to neurons in its vicinity. The CNN is trained using a training set of input data. So, for image processing, the input data may include a set of labeled images. After training is complete, the CNN is configured to analyze a new, unlabeled (or unknown) image, and determine what the image is, a process known as inference. In some embodiments, the inference may be associated with a confidence level or score.

The term convolution refers to the filtering process that happens at the convolution layer. The convolution layer takes a filter (also called a kernel) over an array of image pixels. This creates a convolved feature map, which is an alteration of the image based on the filter. In the convolutional layer, a convolution is applied to the input using a receptive field. The convolution layer receives input from a portion of the previous layer, where the portion is the receptive field, and applies a filter to the receptive field, to find features of an image. The convolution is the repeated application of the filter over the receptive field.

The features in the convolutional layers and the voting weights in the fully connected layers may be learned by backpropagation (or, in some embodiments, forward propagation). The voting weights can thus be set to any value initially. For each feature pixel and voting weight, adjustments up and down are made to see how the error changes. The error signal helps drive a process known as gradient descent. The ability to do gradient descent is very special feature of CNNs. Each of the feature pixels and voting weights are adjusted up and down by a very small amount to see how the error changes. The amount they're adjusted is determined by how big the error is. Doing this over and over helps all of the values across all the features and all the weights settle in to a minimum to train the CNN.

Other examples of the present disclosure may include any number and combination of computational models having any number and combination of characteristics. The computational model(s) can be trained in a supervised, semi-supervised, or unsupervised manner, or any combination of these. The computational model(s) can be implemented using a single computing device or multiple computing devices.

In some embodiments, BG status information 138 may include a BG status of patient 150 determined via the BG monitoring process. In some embodiments, BG status information 138 may include predicted or estimated information, for example, a predicted status in a future time span. In some embodiments, the time span may be or may include about 30 seconds, about 1 minute, about 2 minutes, about 5 minutes, about 10 minutes, about 15 minutes, about 30 minutes, about 1 hour, about 2 hours, about 5 hours, about 10 hours, and any value or range between any two of these values (including endpoints). For example, BG status information 138 may indicate a prediction of a normal status over the time span (for example, no hypoglycemic events imminent within the time span). BG status information 138 may indicate a prediction of an abnormal status over the time span, such as a low BG episode, a high BG episode, a hypoglycemic episode, a hyperglycemic episode, and/or the like.

Diabetes management logic 122, for example, implemented via diabetes management application 140 being executed by processor circuitry 120, may operate to perform a BG monitoring process and/or an insulin infusion process according to some embodiments.

Figure 3:
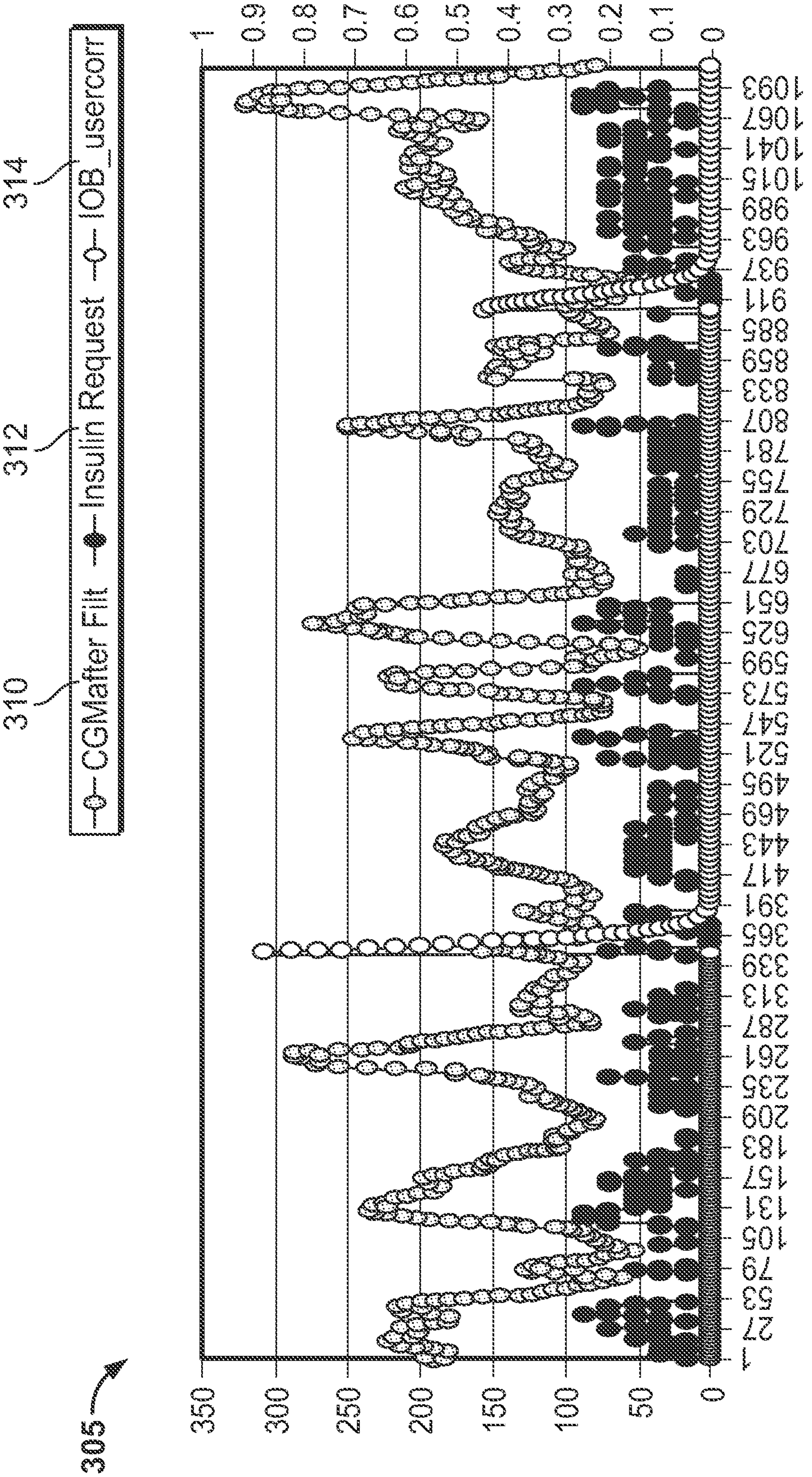
FIG. 3 illustrates a first patient monitoring information structure in accordance with the present disclosure.

For example, diabetes management application 140 may operate to access monitoring information 134 and generate a monitoring information structure. For example, access monitoring information 134 in the form of historical CGM, BG concentration, insulin dosages, IOB information, and/or the like may be transformed into a graph information structure. FIG. 3 illustrates a patient monitoring information structure in accordance with the present disclosure. As shown in FIG. 3, graph 305 visually depicts historical information for CGM (BG concentration information) 310, insulin dosage (for instance, insulin volume infused at a particular time) 312, and IOB information 314. In general, IOB information 314 may be determined using IOB calculation processes known to those of skill in the art. Although CGM information, insulin dosage information, and/or IOB information are used as illustrative monitoring information in the present disclosure, embodiments are not so limited, as any other type of information that may be used to determine BG status information (for instance, heart rate, temperature, illness condition, activity level, carbohydrate intake, and/or the like) is contemplated herein.

Figure 4:
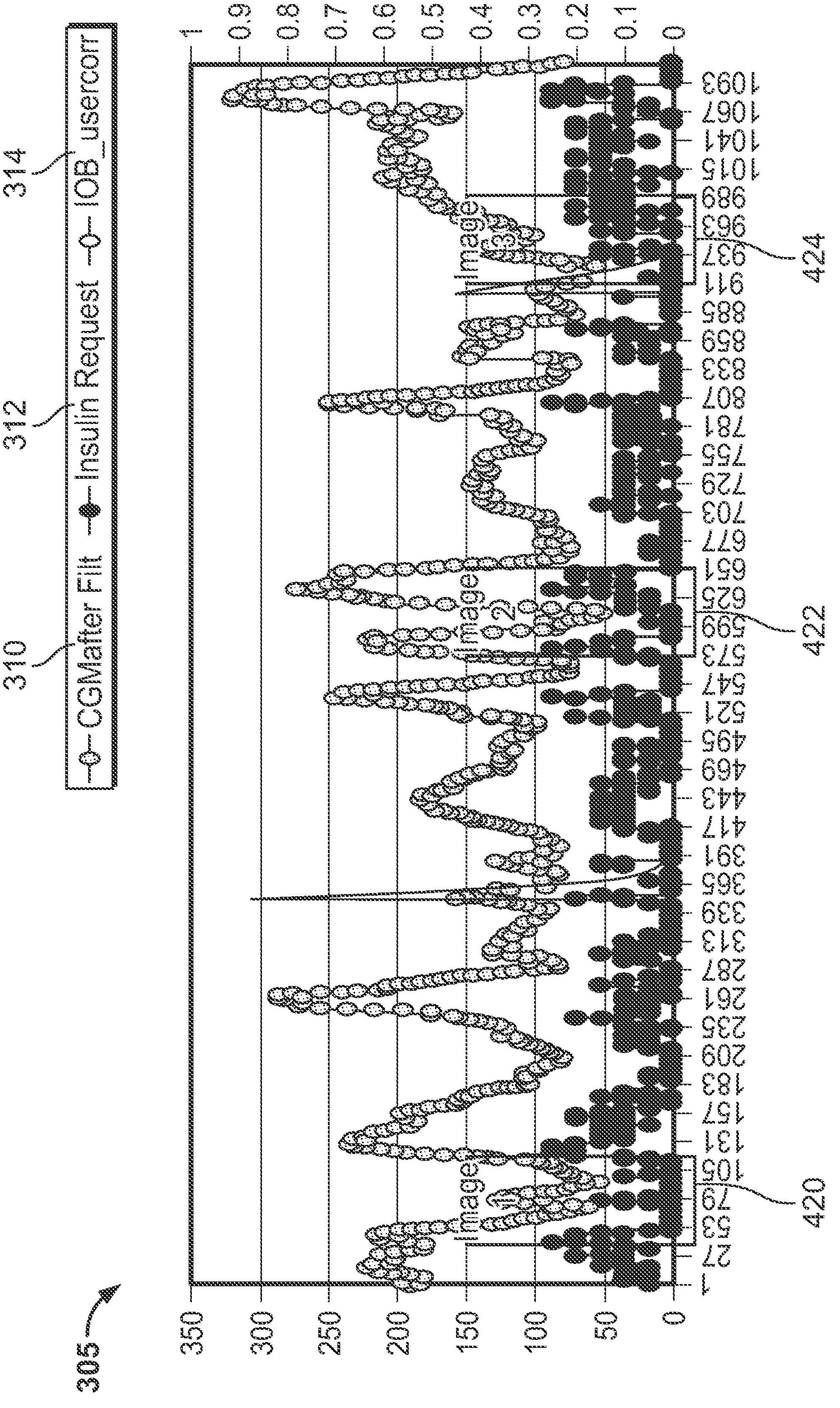
FIG. 4 illustrates patient monitoring images based on the monitoring information structure of FIG. 3 in accordance with the present disclosure.

In various embodiments, diabetes management application 140 may transform the monitoring information structure into one or more visual images. FIG. 4 illustrates patient monitoring images based on the monitoring information structure of FIG. 3 in accordance with the present disclosure. As shown in FIG. 4, images 420, 422, and 424 may be generated based on information structured in graph 305. In the example of FIG. 4, images 420, 422, and 424 represent hypoglycemic episodes of an individual (which may or may not be historical information of patient 150). In some embodiments, images 420, 422, and 424 may be a region of interest (ROI), such as a predefined duration (for instance, a 5 minute time span), or may be selected to cover certain information, such as a drop in BG of over 20 mg/dL.

Figure 5:
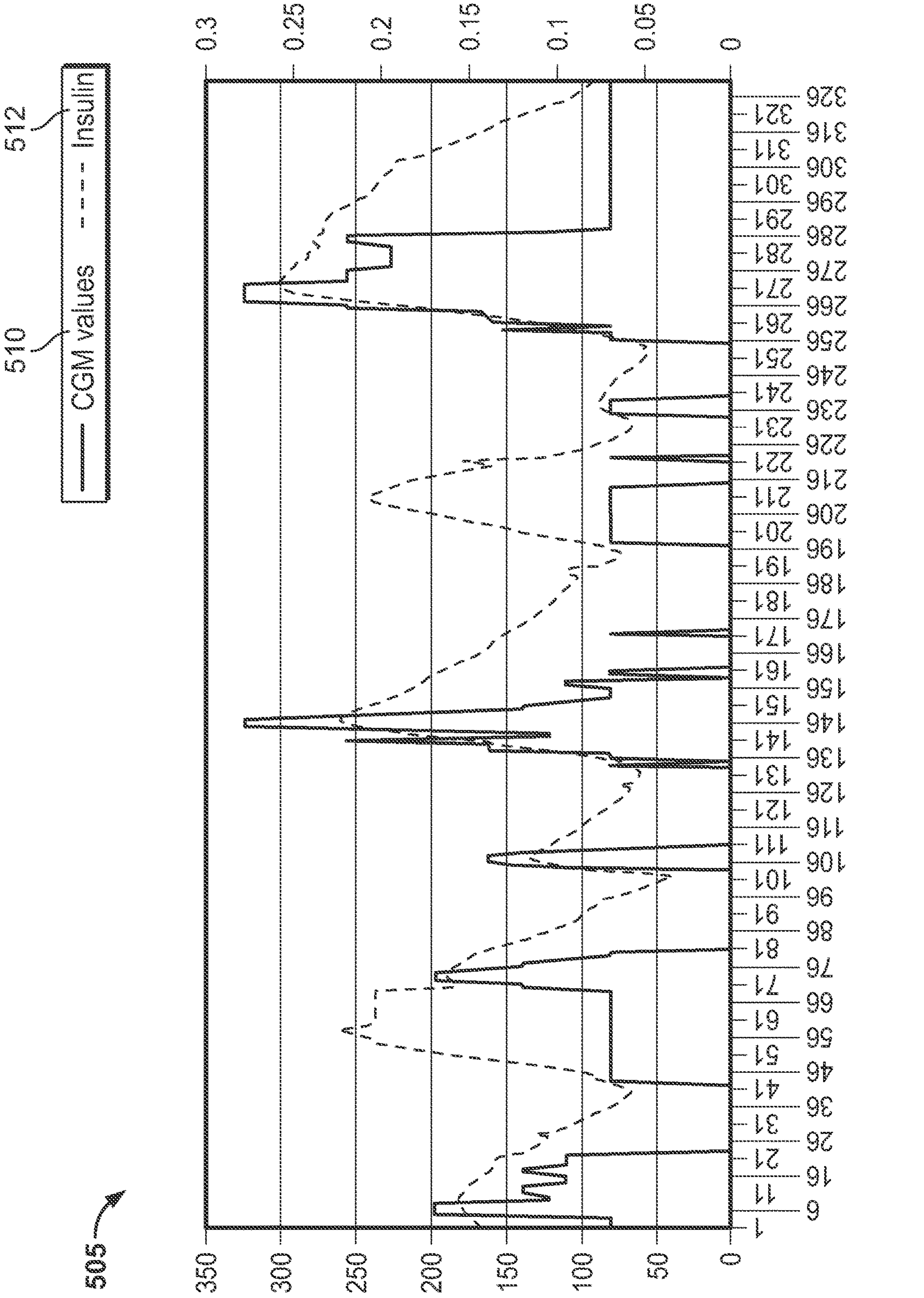
FIG. 5 illustrates a second patient monitoring information structure in accordance with the present disclosure.
Figure 6:
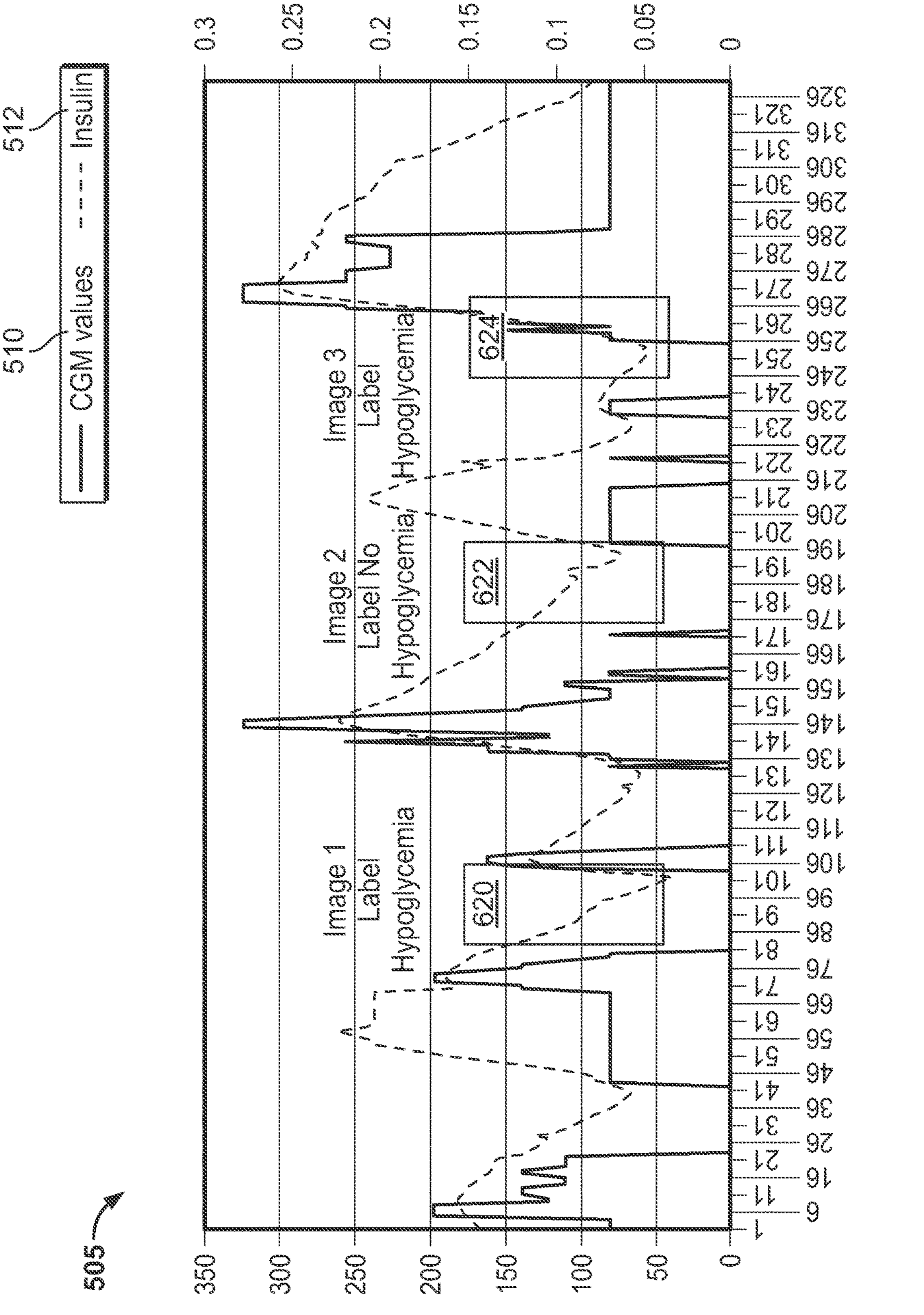
FIG. 6 illustrates patient monitoring images based on the monitoring information structure of FIG. 5 in accordance with the present disclosure.

FIG. 5 illustrates a patient monitoring information structure in accordance with the present disclosure. As shown in FIG. 5, graph 505 visually depicts historical information for CGM (BG concentration information) 510 and insulin (for instance, insulin dosage or volume infused at a particular time) 512. In various embodiments, diabetes management application 140 may transform the monitoring information structure into one or more visual images. FIG. 6 illustrates patient monitoring images based on the monitoring information structure of FIG. 5 in accordance with the present disclosure. As shown in FIG. 6, images 620, 622, and 624 may be generated based on information structured in graph 505. In the example of FIG. 6, images 620, 622, and 624 represent hypoglycemic episodes of an individual (which may or may not be historical information of patient 150). In some embodiments, images 620, 622, and 624 may be a ROI or may be selected to cover certain information or events (e.g., BG drop over a threshold amount, BG below a threshold amount for a threshold duration, etc.).

Images, such as images 420, 422, 424, 620, 622, and 624, may include visual images, such as digital images, electronic images, and/or the like, for example, stored as monitoring information 134. Images 420, 422, 424, 620, 622, and 624 may be stored as electronic image or video files, including, without limitation, *.mp3, *.mp4, *.avi,*.jpg, *.png, *.bmp, *.tif, and/or the like formats. Images 420, 422, 424, 620, 622, and 624 may include pixel information, color information, and/or other image information that may be extracted and used to train computational models according to some embodiment. For example, to train on hypoglycemic episodes, image information from actual hypoglycemic episodes may be extracted and analyzed. To train on other BG conditions (for instance, normal, high BG, low BG, hyperglycemic, and/or the like), images may be taken from true episodes that have happened in the past. Images that are not related to a particular BG condition may also be used for model training, for example, to demonstrate true negatives. Accordingly, images 420, 422, 424, 620, 622, and 624 may be used to train a computational model to recognize positive hypoglycemic episodes and other images, for example, from FIGS. 3 and 5, outside of the areas bounded by 420, 422, 424, 620, 622, and 624 may be used to train on negative episodes.

In addition, images the same or similar to images 420, 422, 424, 620, 622, and 624 (or other images of patient 150) may be analyzed by computational models of computational model information 136 to generate a BG status of BG status information 138.

In some embodiments, BG status information 140, such as a predicted hypoglycemic event, may be used to control AID device 160. For example, an infusion volume or infusion rate of AID device 160 may be modified based on BG status information 138 (for example, indicating an imminent hypoglycemic event). In various embodiments, diabetes management application 140 may generate a message or alert indicating a BG status. For example, for an abnormal status, diabetes management application 140 may cause computing device 110 may provide an alert, such as a visual message on display device, an auditory alert, a haptic alert, and/or the like. In another example, for a normal status, diabetes management application 140 may cause computing device 110 to display a message indicating that BG levels are within a normal range. Embodiments are not limited in this context.

Figure 2:
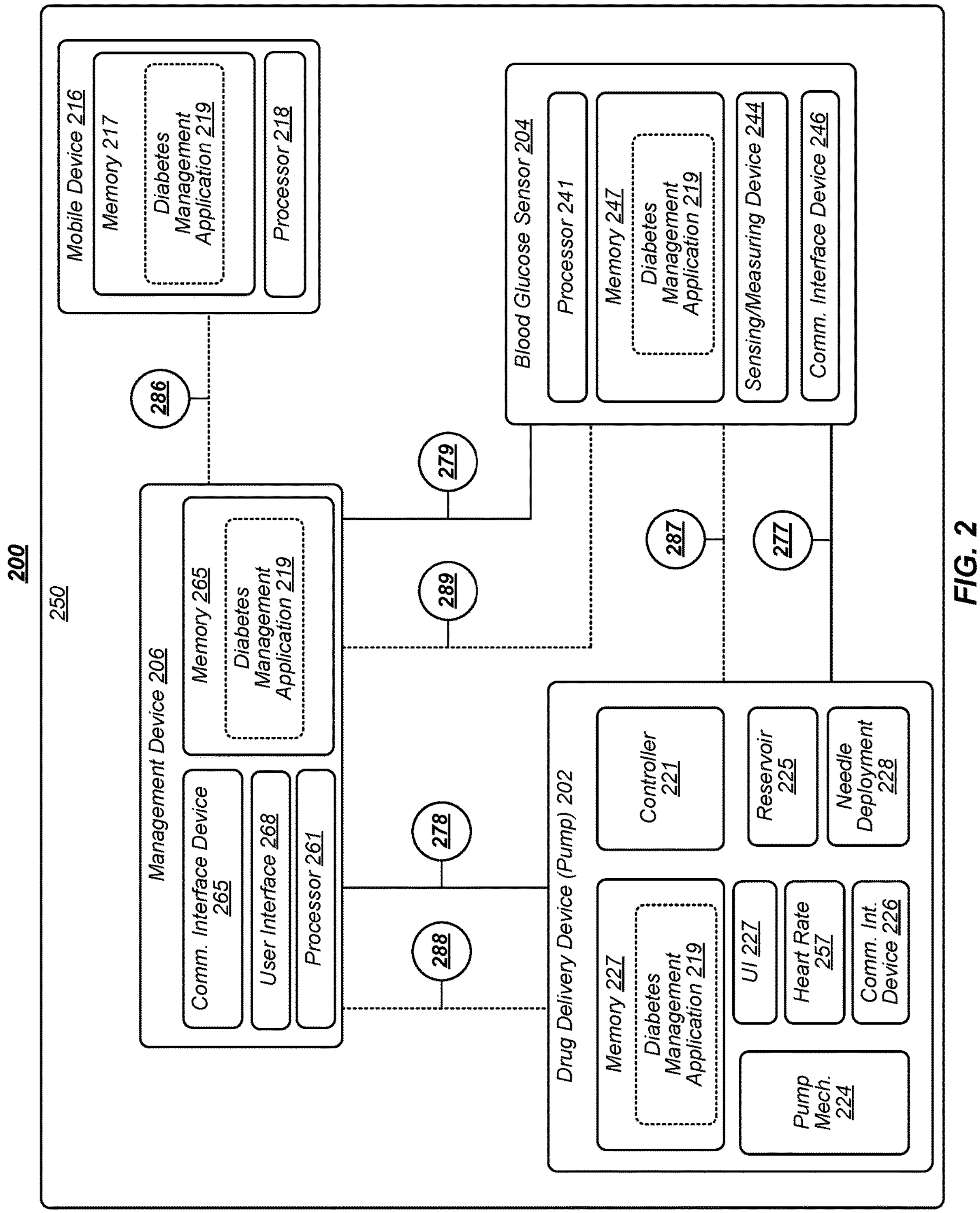
FIG. 2 illustrates a second exemplary operating environment in accordance with the present disclosure.

FIG. 2 illustrates a second exemplary operating environment in accordance with the present disclosure. More specifically, FIG. 2 illustrates an example of an operating environment 200 implementing a drug delivery system that utilizes one or more examples of the BG monitoring process according to some embodiments, for example, as described with reference to FIGS. 1 and 8-11. In some embodiments, drug delivery system 250 may be an implementation of operating environment 100 of FIG. 1 (or vice versa).

As shown in FIG. 2, drug delivery system 250 may include a drug delivery device 202, a management device 206, and a blood glucose sensor 204. In some embodiments, drug delivery device 202 may be a wearable or on-body drug delivery device that is worn on the body of a patient or user. Drug delivery device 202 may include a pump mechanism 224 that may, in some examples be referred to as a drug extraction mechanism or component, and a needle deployment component 228. In various examples, the pump mechanism 224 may include a pump or a plunger (not shown).

Needle deployment component 228 may, for example, include a needle (not shown), a cannula (not shown), and any other fluid path components for coupling the stored liquid drug in reservoir 225 to the user. The cannula may form a portion of the fluid path component coupling the user to reservoir 225. After needle deployment component 228 has been activated, a fluid path (not shown) to the user is provided, and pump mechanism 224 may expel the liquid drug (for instance, insulin) from reservoir 225 to deliver the liquid drug to the user via the fluid path. The fluid path may, for example, include tubing (not shown) coupling wearable drug delivery device 202 to the user (e.g., tubing coupling the cannula to reservoir 225).

Wearable drug delivery device 202 may further include a controller 221 (for instance, the same or similar to processing circuitry 120) and a communications interface device 226. Controller 221 may be implemented in hardware, software, or a combination thereof. The controller 221 may, for example, be a processor, a logic circuit or a microcontroller coupled to a memory 223. Controller 221 may maintain a date and time as well as other functions (e.g., calculations or the like) performed by processors. Controller 221 may be operable to execute an AP or AID application, for example, diabetes management application 219 stored in memory 223 that enables controller 221 to direct operation of drug delivery device 202. In addition, controller 221 may be operable to receive data or information indicative of physiological characteristics of the user from mobile device 216, blood glucose sensor 205, management device 206, and/or the like.

In some embodiments, drug delivery device 202 may include or may be communicatively coupled to a blood glucose sensor 204. In some embodiments, blood glucose sensor 204 may be a CGM sensor. In various embodiments, blood glucose sensor 204 may be a fingerstick-based blood glucose sensor. Blood glucose sensor 204 may be physically separate from drug delivery device 202 or may be an integrated component thereof. In various embodiments, blood glucose sensor 204 may provide controller 221 with data indicative of measured or detected blood glucose (BG) levels of the user. In some embodiments, a user may manually enter blood glucose measurements, for instance, measured via a fingerstick method into management device 205, mobile device 216, drug delivery device 202, and/or management device 206 for use by drug delivery device 202.

Management device 206 (for instance, a PMD) may be maintained and operated by the user or a caregiver of the user. Management device 206 may control operation of drug delivery device 202 and/or may be used to review data or other information indicative of an operational status of drug delivery device 202 or a status of the user. Management device 206 may be used to direct operations of drug delivery device 202. For example, management device 206 may be a dedicated personal diabetes management (PDM) device, a smartphone, a tablet computing device, other consumer electronic device including, for example, a desktop, a laptop, a tablet, or the like. Management device 206 may include a processor 261 and memory devices 263. In some embodiments, memory devices 263 may store a diabetes management application 219 that may be or may include an AP or AID application including programming code that may implement delivery of insulin based on input from blood glucose sensor 204 (for instance, via a CGM-based blood glucose sensor 204 and/or a fingerstick-based blood glucose sensor 204) and/or manual user input.

In some embodiments, management device 206 may operate in cooperation with a mobile device 216. In various embodiments, mobile device 216 may include a memory 213 and a processor 218 as well as additional components and elements as discussed with reference to computing device 110 of FIG. 1. Memory 213 may store programming code as well as mobile computer applications, such as diabetes management application 219.

In an example, wearable drug delivery device 202 may be attached to the body of a user, such as a patient or diabetic, and may deliver any therapeutic agent, including any drug or medicine, such as insulin or the like, to a user. Wearable drug delivery device 202 may, for example, be a wearable device worn by the user. For example, wearable drug delivery device 202 may be directly coupled to a user (e.g., directly attached to a body part and/or skin of the user via an adhesive or the like). In an example, a surface of the wearable drug delivery device 202 may include an adhesive to facilitate attachment to a user. Wearable drug delivery device 202 may be referred to as a pump, or an insulin pump, in reference to the operation of expelling a drug from reservoir 225 for delivery of the drug to the user.

In an example, wearable drug delivery device 202 may include a reservoir 225 for storing the drug (such as insulin), a needle or cannula (not shown) for delivering the drug into the body of the user (which may be done subcutaneously, intraperitoneally, or intravenously), and a pump mechanism 224, or other drive mechanism, for expelling the stored insulin from the reservoir 225, through a needle or cannula (not shown), and into the user. Reservoir 225 may be operable to store or hold a liquid or fluid, such as insulin or another therapeutic drug. Pump mechanism 224 may be fluidly coupled to reservoir 225, and communicatively coupled to controller 221. Wearable drug delivery device 202 may also include a power source (not shown), such as a battery, a piezoelectric device, or the like, for supplying electrical power to pump mechanism 224 and/or other components (such as controller 221, memory 223, and communication interface device 226) of wearable drug delivery device 202.

In an example, blood glucose sensor 204 may be a CGM device communicatively coupled to the processor 261 or 221 and may be operable to measure a blood glucose value at a predetermined time interval, such as approximately every 5 minutes, or the like. Blood glucose sensor 204 may provide a number of blood glucose measurement values to the diabetes management application 219 operating on the respective devices. In another example, blood glucose sensor 204 may be a manual blood glucose sensor measuring blood glucose in blood from a fingerstick method.

Wearable drug delivery device 202 may operate to provide insulin stored in reservoir 225 to the user based on information (for instance, BG monitoring information 138) determined via a BG monitoring process and/or an insulin infusion process according to some embodiments. For example, wearable drug delivery device 202 may contain analog and/or digital circuitry that may be implemented as a controller 221 (or processor) for controlling the delivery of the drug or therapeutic agent. The circuitry used to implement controller 221 (the same or similar to processing circuitry 120) may include discrete, specialized logic and/or components, an application-specific integrated circuit, a microcontroller or processor that executes software instructions, firmware, programming instructions or programming code (for example, diabetes management application 140 as well as the process examples of FIGS. 7-10) stored in memory 223, or any combination thereof. For example, controller 221 may execute a control algorithm, such an AID algorithm of diabetes management application 219, that may make the controller 221 operable to cause pump mechanism 224 to deliver doses of the drug or therapeutic agent to a user at predetermined intervals or as needed to bring blood glucose measurement values to a target blood glucose value based on the insulin infusion process according to some embodiments.

The devices in system 250, such as management device 206, wearable drug delivery device 202, and sensor 204, may also be operable to perform various functions including controlling wearable drug delivery device 202. For example, management device 206 may include a communication interface device 264, a processor 261, and a management device memory 263. In some embodiments, management device memory 263 may store an instance of diabetes management application 219.

In some embodiments, sensor 204 of system 250 may be a continuous glucose monitor (CGM) or a manual glucose sensor, that may include a processor 241, a memory 243, a sensing or measuring device 244, and/or a communication interface device 246. Memory 543 may store an instance of diabetes management application 219 as well as other programming code and may be operable to store data related to diabetes management application 219.

Instructions for determining the delivery of the drug or therapeutic agent (e.g., as a bolus dosage) to the user (e.g., the size and/or timing of any doses of the drug or therapeutic agent) may originate locally by wearable drug delivery device 202 or may originate remotely and be provided to wearable drug delivery device 202. In an example of a local determination of drug or therapeutic agent delivery, programming instructions, such as an instance of the diabetes management application 219, stored in the memory 223 that is coupled to wearable drug delivery device 202 may be used to make determinations by wearable drug delivery device 202. In addition, wearable drug delivery device 202 may be operable to communicate via communication interface device 226 and wireless communication link 288 with wearable drug delivery device 202 and with blood glucose sensor 204 via communication interface device 226 and wireless communication link 289.

In addition or alternatively, remote instructions may be provided to wearable drug delivery device 202 over a wired or wireless link by the management device (PDM) 206. For example, PDM 206 may be equipped with a processor 261 that may execute an instance of the diabetes management application 219 resident in the memory 263. Wearable drug delivery device 202 may execute any received instructions (originating internally or from management device 206) for the delivery of insulin to the user. In this manner, the delivery of the insulin to a user may be automated.

Devices within insulin delivery system 250 may be configured to communicate via various wired links 277-279 and/or wireless links 286-289. Wired links 277-279 may be any type of wired link provided by any known or future wired communication standard. Wireless links 286-289 may be any type of wireless link provided by any known or future wireless standard. As an example, wireless links 286-289 may enable communications between wearable drug delivery device 202, management device 206, sensor 204 based, and/or mobile device 216 on, for example, Bluetooth®, Wi-Fi®, a near-field communication standard, a cellular standard, or any other wireless optical or radio-frequency protocol. In some embodiments, mobile device 216 may operate as a management device 206 (for instance, management device 206 may not be a separate PDM device; rather, PDM functions are performed via diabetes management application 219 operating on mobile device 216).

Although sensor 204 is depicted as separate from wearable drug delivery device 202, in various examples, sensor 204 and wearable drug delivery device 202 may be incorporated into the same unit. For example, sensor 204 may be a part of wearable drug delivery device 202 and contained within the same housing of wearable drug delivery device 202. Blood glucose measurement information (whether automatically or manually (fingerstick) determined) determined by sensor 204 may be provided to wearable drug delivery device 202 and/or management device 206, which may use the measured blood glucose values to determine an infusion amount or rate based on an insulin infusion process according to some embodiments.

In some examples, wearable drug delivery device 202 and/or management device 206 may include a user interface 227 and 268, respectively, such as a keypad, a touchscreen display, levers, buttons, a microphone, a speaker, a display, or the like, that is operable to allow for user input and/or output to user (for instance, a display of information).

In some embodiments, drug delivery system 250 may implement an AP or AID algorithm (for instance, diabetes management application 219) to govern or control automated delivery of insulin to a user based on an insulin infusion process according to some embodiments. Diabetes management application 219 may be used to determine the times and dosages of insulin delivery (for example, a rate based on the basal parameter, $I_{add}$, adjustment factors, safety constraints, and/or the like). In various examples, the diabetes management application 219 may determine the times and dosages for delivery based, at least in part, on information known about the user, such as gender, age, weight, height, and/or other information gathered about a physical attribute or condition of the user (e.g., from the sensor 204).

Figure 7:
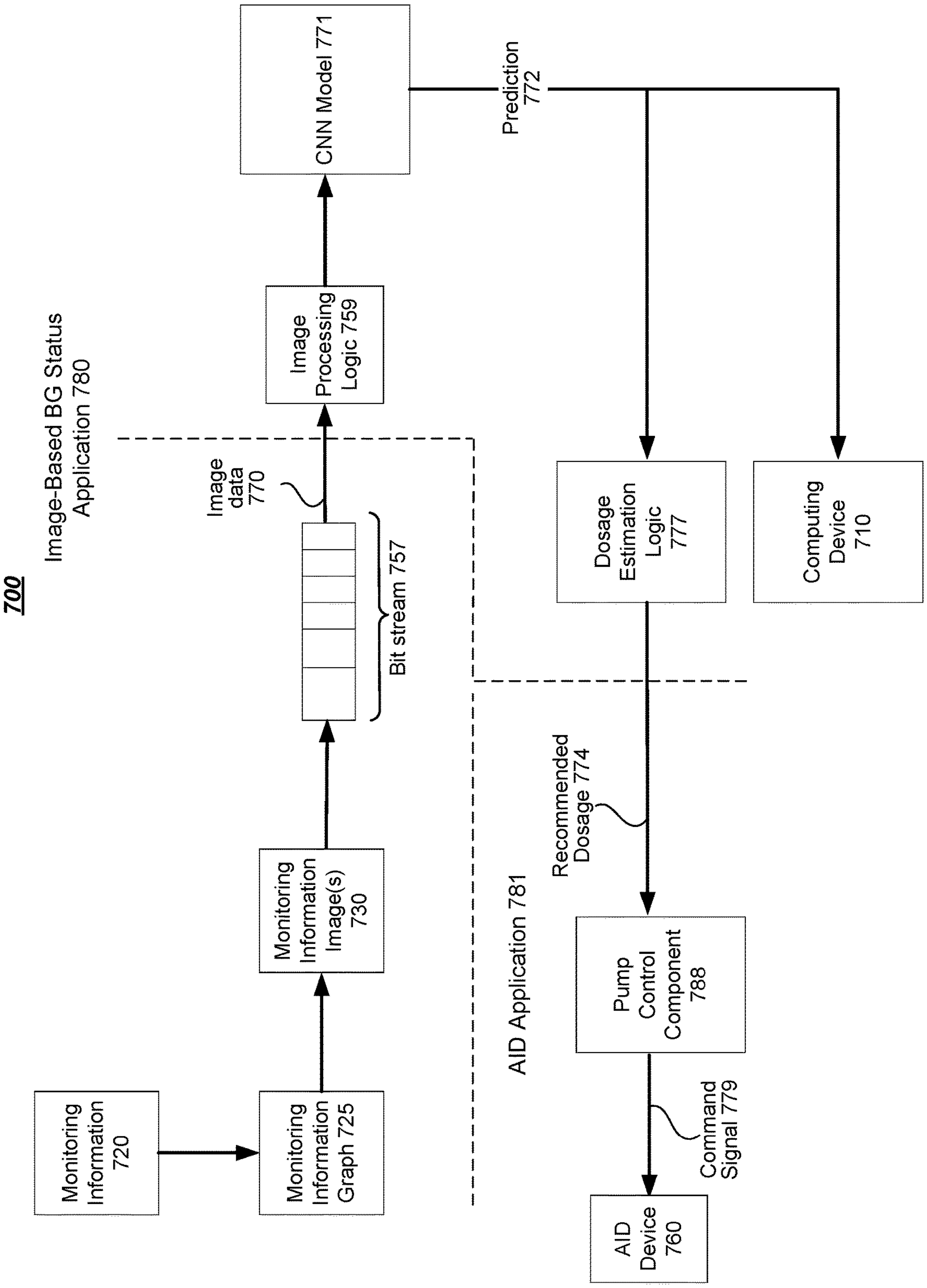
FIG. 7 illustrates a third exemplary operating environment in accordance with the present disclosure.

FIG. 7 illustrates a third exemplary operating environment in accordance with the present disclosure. As shown in FIG. 7, image-based BG status application 780 may transform monitoring information 720 into a monitoring information graph 725 (see, for example, FIGS. 3 and 5). One or more monitoring information images 730 (see, for example, FIGS. 4 and 6) may be generated based on monitoring graph information 725. In some embodiments, images 730 may be of a predefined duration, such as a 5 minute time span, or may be selected to cover certain information, such as a drop in BG of over 20 mg/dL.

Image data 770 may be determined from monitoring information images 730, for example, as a bit stream 757 of image data that is received by image processing logic 759. In some embodiments, image processing logic 759 may operate to analyze image data 770 to extract features to provide to a trained CNN model 771. For example, to train on hypoglycemic episodes, image information from actual hypoglycemic episodes may be extracted and analyzed. For example, image processing logic 759 may operate to obtain image features relevant to analyzing monitoring information images 730, for example, in reference to images 420, 422, and 424 of FIG. 4 or images 620, 622, and 624 of FIG. 6, visual combinations of monitoring information, such as IOB information 314 and CGM information 310 during a hypoglycemic episode. In some embodiments, CNN model 771 may be trained to determine which visual characteristics are most relevant for analyzing image data 770 to make predictions 772.

CNN model 771 may generate a prediction 772 (i.e., status information), such as a prediction that a patient may likely experience normal blood sugar in the time span. In another example, a prediction may indicate that a patient is likely to experience a hypoglycemic event in a certain time span. In some embodiments, CNN model 771 may operate to associated prediction 772 with a confidence indicator (for instance, based on a SoftMax function). For example, CNN model 771 may provide a confidence indicator that is a percentage indicating a level of confidence (for instance, on a scale of 0% (low) to 100% (high)). For example, CNN model 771 may generate a prediction of a hypoglycemic episode within the next 30 minutes with a confidence level of 80%.

In some embodiments, prediction 772 may be provided to a computing device 710 (for instance, the same or similar to computing device 110). In various embodiments, computing device 710 may communicate prediction 772 to user, such as by providing a "normal BG" message or generating a "hypoglycemic episode" alert. In exemplary embodiments, prediction 772 may be provided to dosage estimation logic 777, for example, of an AID application 781. Dosage estimation logic 777 may use prediction 772 to generate a dosage recommendation 774 (for instance, no change in a dosage for a normal prediction, a reduction in a dosage for a hypoglycemic prediction, an increase in a dosage for a hyperglycemic prediction, and/or the like). A pump control component 788 may receive recommended dosage 774 and generate a command signal 779 for AID device 760 to control infusion of insulin into the patient based, at least in part, on prediction 772.

Figure 8:
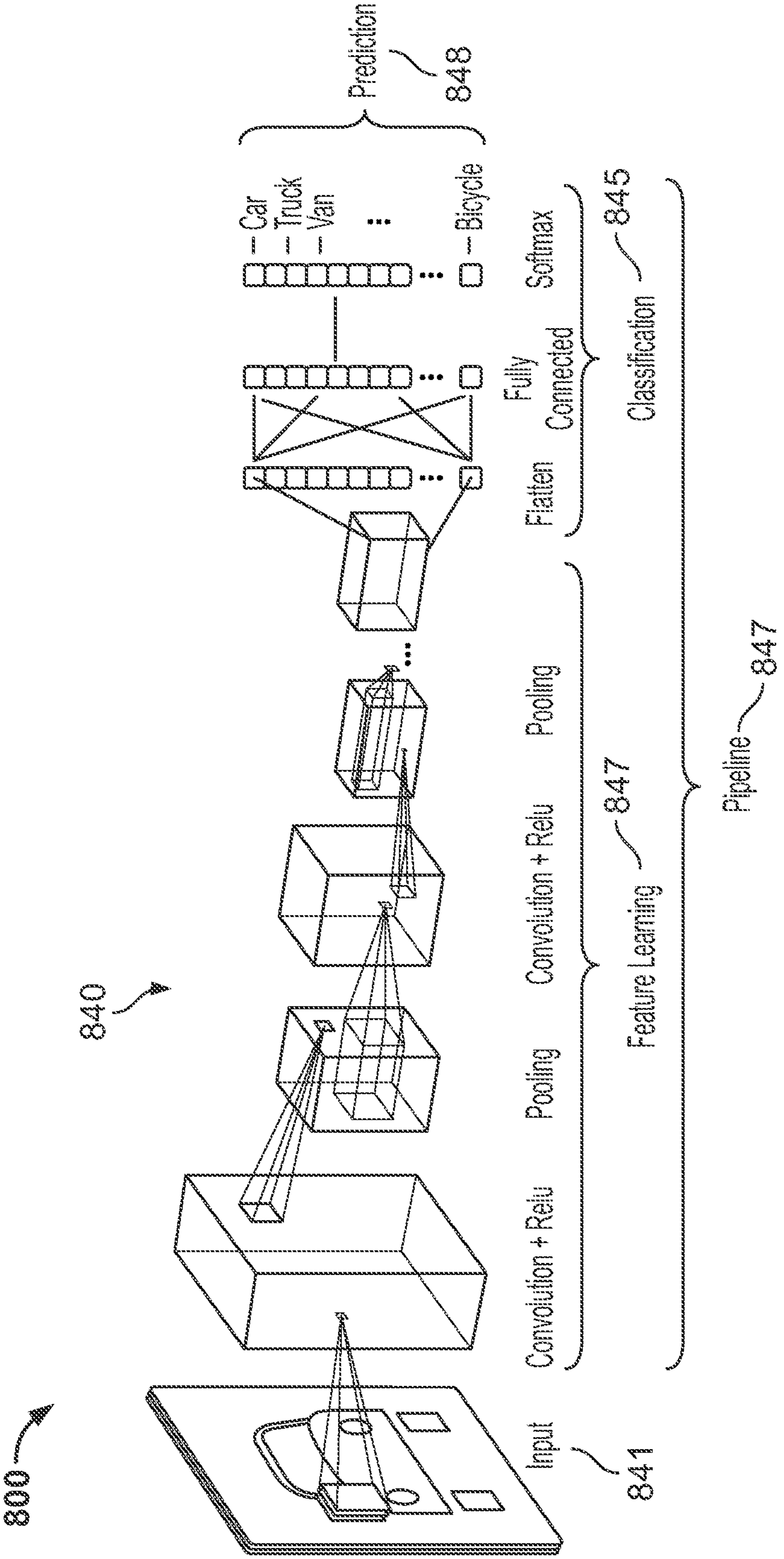
FIG. 8 illustrates a fourth exemplary operating environment in accordance with the present disclosure.

FIG. 8 illustrates a fourth exemplary operating environment in accordance with the present disclosure; As shown in FIG. 8, convolution neural networks, such as 840, may be built to be operable to provide image recognition, image classification, object detection, scene detection, and/or the like. A CNN, such as 840 may be pre-trained so values of the neural network are weighted to be optimally suited to detect BG conditions, such as normal BG conditions, hypoglycemic episodes, hyperglycemic episodes, low BG, high BG, and/or the like. Or, as in the example of FIG. 8, a vehicle. For example, weightings may be applied in the neural network that favor BG conditions of interest. In the example of FIG. 8, the example input image is an automobile, so the weightings of the neural network may be skewed in favor of elements of automobiles, such as edges, cylindrical shapes (i.e., wheels/tires) at the base of the image, and the like.

Input image 841 may have a certain number of picture elements (i.e., pixels) arranged in a two dimensional pixel array, such as X pixels by Y pixels, where X and Y may be the same value or different values. An input image of a BG monitoring process according to some embodiments may include BG monitoring information (for example, images 420, 422, and 424 of FIG. 4 or images 620, 622, and 624 of FIG. 6). For example, each of the individual pixel in the X by Y pixel array may also have a specific value, such as 0-255 or 0-65535, or the like. The pixel values of the image may be input into the CNN model (for instance, a BG condition model). The image may, for example, be scanned "pixel by pixel" and a smaller filter may be applied to a sub-image of the same size, to extract features of the sub-image. As shown in FIG. 8, various layers within image pipeline 847 of convolutional neural network 840 may extract other information from the inputted image data, and the "pre-trained" network generates an output with a probability of a recognized object. In such an example, the received image may be passed through pipeline 847 (including the components: feature learning 843 and classification 845). Feature learning 843 and classification 845 components of pipeline 847 may provide various operations such as filtering of the image for feature extraction from edges, curves, or the like, as well as the feature learning and classification. One or more feature learning operations may be applied during feature learning 843. In the example, feature learning 843 layer may include a repetitive implementation of convolution and activation functions, such as a rectified linear unit, a bipolar rectified linear unit, a parametric rectified linear unit, a Gaussian error linear unit, or the like. As shown in feature learning 843 layer, a first convolution with activation (i.e., ReLU) operation may be applied to pixel values within a segment of the image, and the results of the first convolution and activation operation may be "pooled" in a sub-image (an image having smaller dimensions than a prior input image or sub-image) by a first pooling operation. The first convolution and activation operation and first pooling operation may be followed by a second convolution with activation (i.e., RELU) operation and a second pooling operation before application of a classification 845 layer. In the example of FIG. 8, feature learning 843 layer is shown with only two implementations of convolution and activation operations and pooling operations, however, more or less convolution and activation operations and pooling operations may be implemented depending upon the degree of granularity and/or the amount of available computing resources. For example, if the CNN processing is performed by a cloud-based service, a greater number of convolution and activation operations and pooling operations may be implemented than when a mobile device, such as a PDM 206, performs the image recognition because the cloud-based system may have access to computing resources with greater processing power. As shown in FIG. 8, pipeline 847 may provide an output 848 that includes a probability of a recognized object. For example, output 848 may be a list of possible classifications of input image 841 with respective probabilities of each being the actual object in image 851. In a further example, output 848 may be presented on a display device which enables a user to select via a user interface multiple objects detected from the input image 841 for example, to select an indicated BG condition. The recognized objects with the highest probabilities may be considered predicted objects and may be the prediction output 848.

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 9:
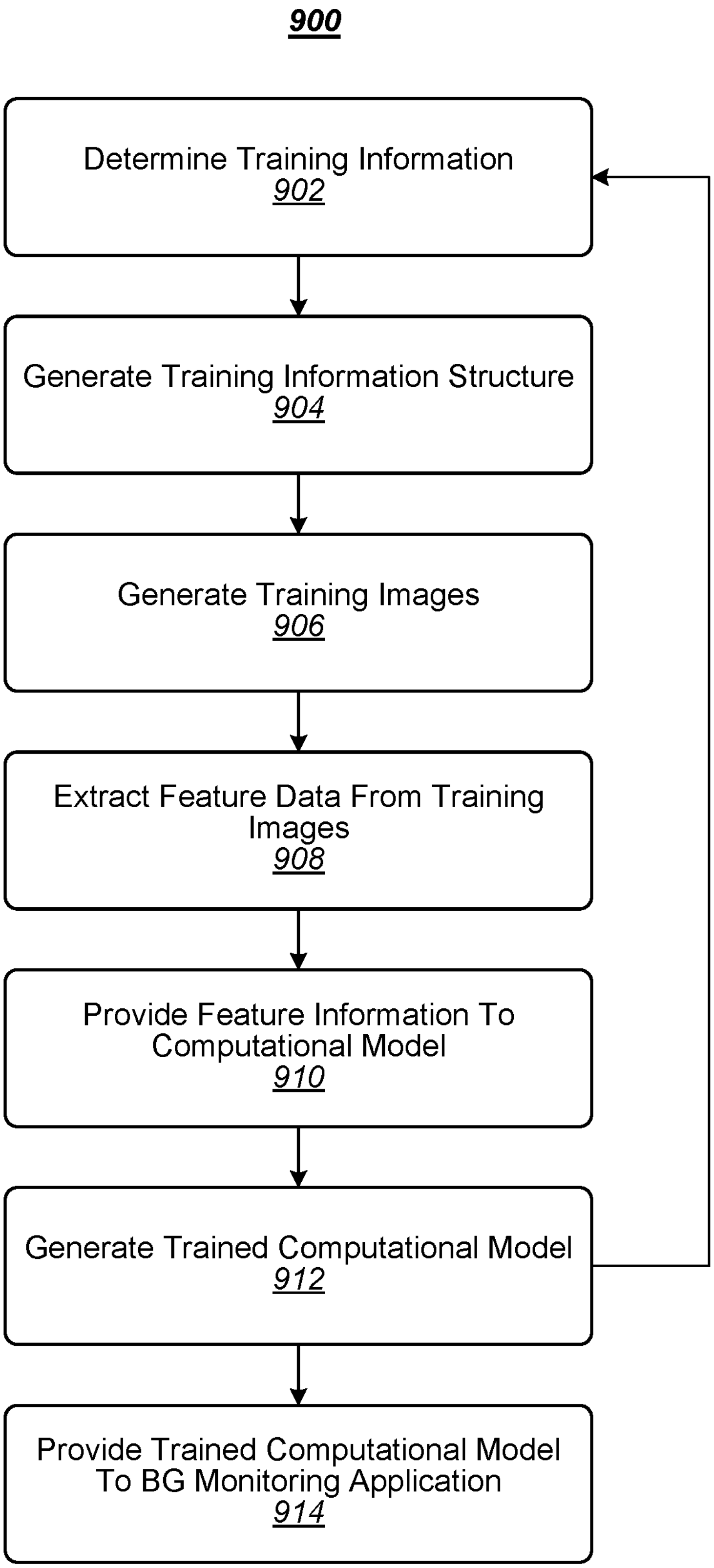
FIG. 9 illustrates a first logic flow in accordance with the present disclosure.

FIG. 9 illustrates an embodiment of a logic flow 900. Logic flow 900 may be representative of some or all of the operations executed by one or more embodiments described herein, such as devices of operating environments 100, 200, 700, and/or 800. In some embodiments, logic flow 900 may be representative of some or all of the operations of training a computational model to operate according to a BG monitoring process.

At block 902, logic flow 900 may include determining training patient monitoring information. For example, BGM monitoring information associated with a patient and/or a population of individuals may be obtained. The BGM monitoring information may include various monitored information, such as BG information (for instance, CGM information), insulin dosage values, IOB values, and/or the like. At block 904, logic flow 900 may generate training information structures. For example, the BGM monitoring information may be transformed into information structures, such as graphs, tables, matrices, and/or the like. Logic flow 900 may generate training images at block 906. For example, images may be generated from the information structures to be used as training information (for instance, the same or similar to input 841 of FIG. 8).

At block 908, logic flow 900 may extract feature data from training images. For example, features specified (or determined via CNN training) to be relevant to determining a BG status of interest may be extracted from the training images. Logic flow 900 may provide the feature information to a computational model at block 910. For example, a data stream of extracted image information may be provided to a CNN model for training. At block 912, logic flow 900 may generate a trained computational model 912. For example, a CNN model may be trained with image data until a certain level of predictive confidence is obtained for predicting BG statuses based on image data of input BG information images. At block 914, the trained computational model may be provided to a BG monitoring application. For example, a trained CNN model may be stored as computational model information 136 for use by diabetes management application 140. In some embodiments, as shown in FIG. 9, the training process implemented by logic flow 900 may be repeated to continually train the computational models.

In some embodiments, the training information may be based on real-time or substantially real-time information (for instance, from monitoring patient 150). In this manner, for an individual, real-time trending data may be used to increase the accuracy of the prediction. For instance, a hypoglycemic episode may be predicted for a patient within a 30-minute time span. Information for the actual BG condition of the patient over this time span may be used to update/re-train the computational model. In some embodiments, if the real-time monitoring information cannot be obtained (for instance, a connection with a CGM sensor is lost), information may be pulled from cloud or other remote source. For example, In this case if the cloud or other remote-based service can read the readings and the image based model is being executed on the cloud, there can be a warning issued to the user about a BG condition through another pathway (for instance, cloud service to smartphone).

In an example, a CNN development and training process for predicting a hypoglycemic episode may include: generating training images, for instance, starting with an image of a CGM trend from 150 to 50 mg/dL as a downward trajectory; applying a filter (or kernel) to extract a feature map, for instance, with a special filter for trending hypoglycemic (i.e., looking for a steep curve with likely (or unlikely) imminent hypoglycemia condition); apply a pooling layer to get condensed representation by pooling various sub-images; flattening the pooled images into a single vector; provide the vector data to the CNN, which applies predetermined "voting" classes to identify class; train the CNN using forward propagation and backpropagation for many iterations (e.g., the forward and backward propagation allows network to output weights and propagate errors back to tune the weights to get correct desired class of the output; the trained CNN has an output that is a confidence level of an imminent hypoglycemic episode.

Figure 10:
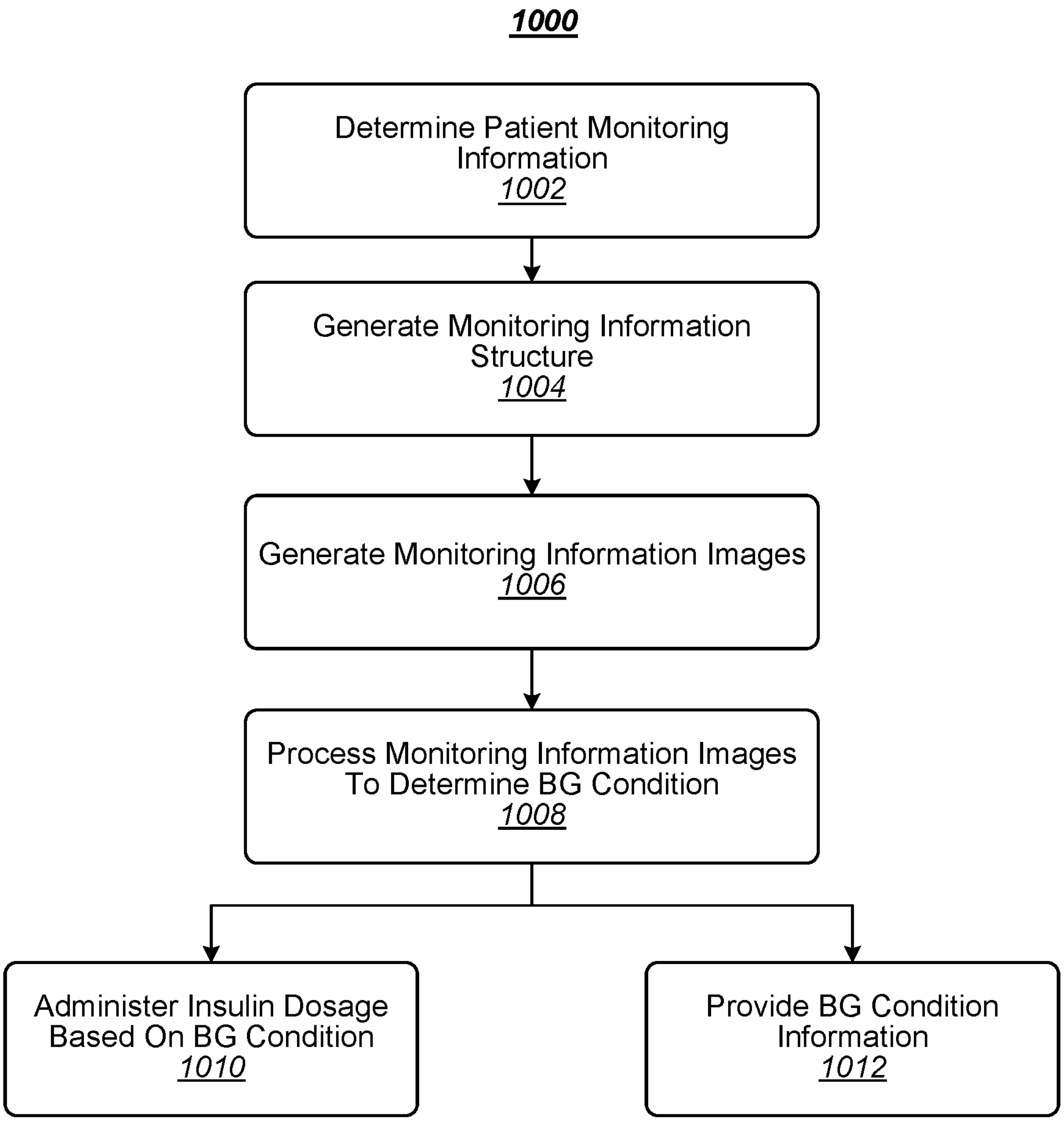
FIG. 10 illustrates a second logic flow in accordance with the present disclosure.

FIG. 10 illustrates an embodiment of a logic flow 1000. Logic flow 1000 may be representative of some or all of the operations executed by one or more embodiments described herein, such as devices of operating environments 100, 200, 700, and/or 800. In some embodiments, logic flow 1000 may be representative of some or all of the operations of training a computational model to operate according to a BG monitoring process.

At block 1002, logic flow 1000 may include determining patient monitoring information. For example, diabetes management application 140 may access monitoring information 134, such as raw (or semi-raw) BG information (for instance, measured via sensors 162*a-n* and/or BG meter 165), insulin dosage information (for instance, historical insulin infusion information), IOB information, and/or the like. Logic flow 1000 may generate monitoring information structures at block 1004. For example, diabetes management application 140 may generate a graph of monitored information, such as graph 305 of FIG. 3 or graph 505 of FIG. 5. At block 1006, logic flow 1000 may generate monitoring information images. For example, diabetes management application 140 may operate to transform monitoring information structures into images, such as digital image files. For example, diabetes management application 140 may or may not cause graph 305 to be converted to a digital image file stored as monitoring information 134. In some embodiments, the images may be of a predefined duration, such as a 5 minute time span, or may be selected to cover certain information, such as a drop in CGM of over 20 mg/dL.

At block 1008, logic flow 1000 may process monitoring information images to determine a BG condition. For example, one or more images may be input into a CNN of computational model information 136 to generate a prediction (or a confidence level) of a BG condition, such as a hypoglycemic episode. Logic flow 1000 may administer an insulin dosage based on the BG condition at block 1010. For example, diabetes management application 140 and/or an AID application may operate to control insulin infusion into patient 150 via AID device 160. Diabetes management application 140 may operate to provide BG condition information 138 or other signals to control the infusion of insulin via AID device. For instance, if a hypoglycemic episode is predicted over a threshold level of confidence, diabetes management application 140 may instruct AID device to skip or reduce a current, pending or future insulin infusion (bolus or basal). In another instance, if a hyperglycemic episode is predicted over the threshold level of confidence, diabetes management application 140 may instruct AID device to inject a bolus volume of insulin into patient. Logic flow 1000 may provide BG condition information at block 1012. For example, diabetes management application 140 may cause a message, alert, or other signal to be presented to patient 150 or a user indicating the current BG condition. In some embodiments, the message may be provided remotely to a healthcare provider or designated caregiver. For instance, one or more individuals may receive a text message if it is predicted that patient 150 will be experiencing a hypoglycemic episode.

Figure 11:
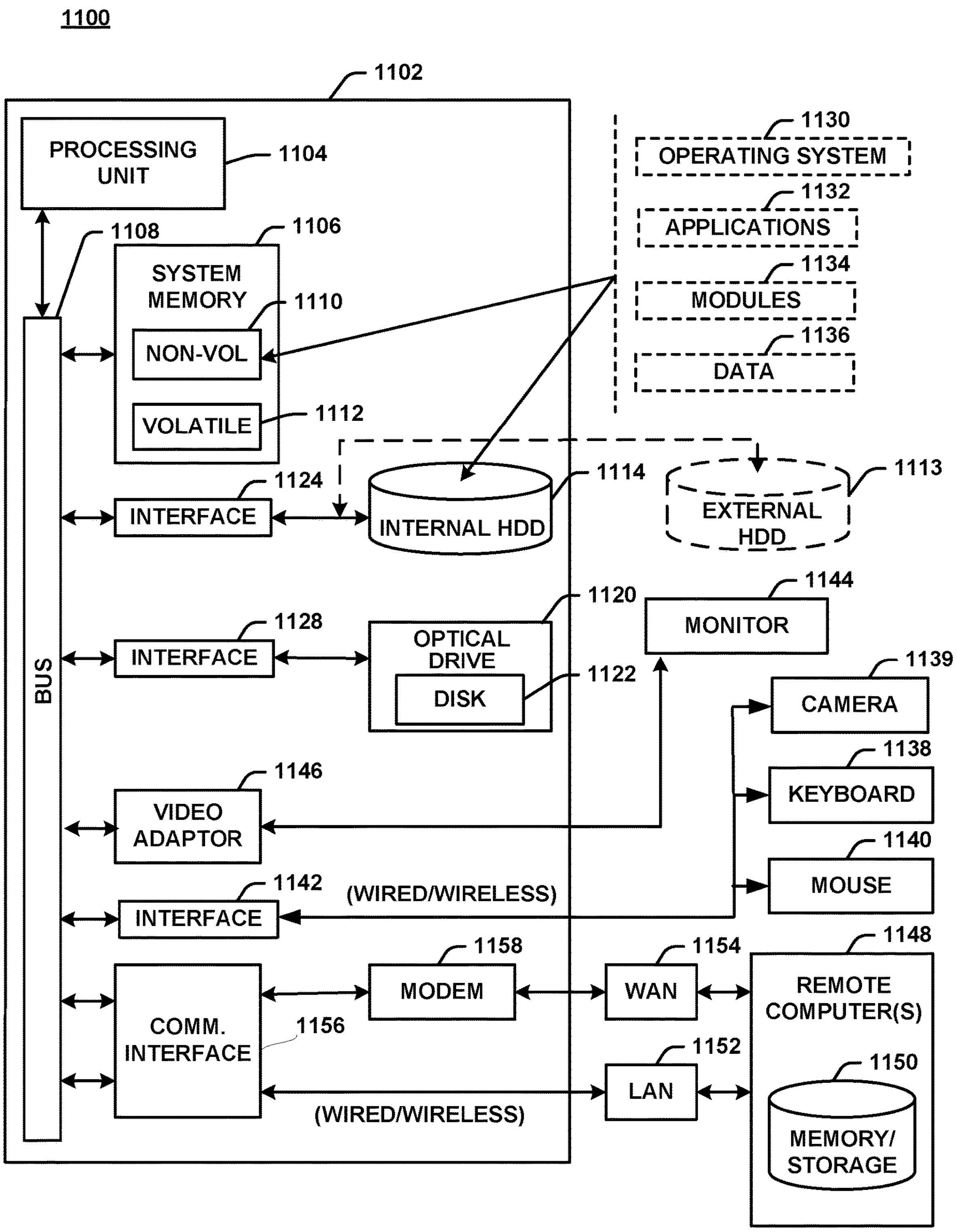
FIG. 11 illustrates an example computer architecture configured to operate as hardware and software components for embodiments of the present disclosure.

FIG. 11 illustrates an example computer architecture configured to operate as hardware and software components for embodiments of the present disclosure. As shown in FIG. 11, the computer architecture 1100 includes a processing unit 1104, a system memory 1106 and a system bus 1108. The processing unit 1104 can be any of various commercially available processors. For example, devices depicted in operating environments 100, 200, 700, and/or 800 may incorporate one or more of the components of the computer architecture 1100, such as the processing unit 1104, the system memory 1106 and so on. Other components, such as the keyboard 1138 and the mouse 1140, may be omitted in some examples.

The system bus 1108 provides an interface for system components including, but not limited to, the system memory 1106 to the processing unit 1104. The system bus 1108 can be any of several types of bus structures that may further interconnect to a memory bus (with or without a memory controller), a peripheral bus, and/or a local bus using any of a variety of commercially available bus architectures. Interface adapters may connect to the system bus 1108 via slot architecture. Example slot architectures may include without limitation Accelerated Graphics Port (AGP), Card Bus, (Extended) Industry Standard Architecture ((E) ISA), Micro Channel Architecture (MCA), NuBus, Peripheral Component Interconnect (Extended) (PCI(X)), PCI Express, Personal Computer Memory Card International Association (PCMCIA), and the like.

The computing architecture 1100 may include or implement various articles of manufacture. An article of manufacture may include a computer-readable storage medium to store logic. Examples of a computer-readable storage medium may include any tangible media capable of storing electronic data, including volatile memory or non-volatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Examples may also be at least partly implemented as instructions contained in or on a non-transitory computer-readable medium, which may be read and executed by one or more processors to enable performance of the operations described herein.

The system memory 1106 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD)) and any other type of storage media suitable for storing information. In the example shown in FIG. 11, the system memory 1106 can include non-volatile memory 1110 and/or volatile memory 1112. A basic input/output system (BIOS) can be stored in the non-volatile memory 1110.

The computer 1102 may include various types of computer-readable storage media in the form of one or more lower speed memory units, including an internal (or external) hard disk drive (HDD) 1114 or 1113, and an optical disk drive 1120 to read from or write to a removable optical disk 1122 (e.g., a CD-ROM or DVD). The HDD 1114 and optical disk drive 1120 can be connected to the system bus 1108 by an HDD interface 1124 and an optical drive interface 1128, respectively. The HDD interface 1124 for external drive implementations can include at least one or both of Universal Serial Bus (USB) and IEEE 1394 interface technologies. The drives and associated computer-readable media provide volatile and/or nonvolatile storage of data, data structures, computer-executable instructions, and so forth. For example, several program modules can be stored in the drives and memory units 1110 and 1112, including an operating system 1130, one or more application programs 1132 (such as an AP application, an image-based bolus estimation application and the like), other program modules 1134, and program data 1136. In one example, the one or more application programs 1132, other program modules 1134, and program data 1136 can include, for example, the various applications (e.g., Bluetooth® transceiver, camera applications and the like) and/or components of the computer architecture 1100.

A user can enter commands and information into the computer 1102 through one or more wired/wireless input devices, for example, a camera 1139, a keyboard 1138 and a pointing device, such as a mouse 1140. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, track pads, sensors, styluses, and the like. The camera 1139, the keyboard 1138 and mouse 1140 as well as the other input devices are often connected to the processing unit 1104 through an input device interface 1142 that is coupled to the system bus 1108 but can be connected by other interfaces such as a parallel port, IEEE 1394 serial port, a game port, a USB port, an IR interface, and so forth.

A monitor 1144 or other type of display device is also connected to the system bus 1108 via an interface, such as a video adaptor 1146. The monitor 1144 may be internal or external to the computer 1102. In addition to the monitor 1144, a computer typically includes other peripheral output devices, such as speakers, printers, and so forth, that are not shown for ease of illustration.

The computer 1102 may operate in a networked environment using logical connections via wired and/or wireless communications to one or more remote computers, such as a remote computer 1148. The remote computer 1148 can be a workstation, a server computer, a router, a personal computer, portable computer, microprocessor-based entertainment appliance, a peer device or other common network node, and typically includes many or all the elements described relative to the computer 1102, although, for purposes of brevity, only a memory/storage device 1150 is illustrated. The logical connections depicted include wired/wireless connectivity to a local area network (LAN) 1152 and/or larger networks, for example, a wide area network (WAN) 1154.

When used in a LAN networking environment, the computer 1102 may be connected to the LAN 1152 through a wired and/or wireless communication interface 1156. The communication interface 1156 can facilitate wired and/or wireless communications to the LAN 1152, which may also include a wireless access point disposed thereon for communicating with the wireless functionality of the communication interface 1156.

When used in a WAN networking environment, the computer 1102 can include a modem 1158, or is connected to a communications server on the WAN 1154 or has other means for establishing communications over the WAN 1154, such as by way of the Internet. The modem 1158, which can be internal or external and a wire and/or wireless device, connects to the system bus 1108 via the input device interface 1142. In a networked environment, program modules depicted relative to the computer 1102, or portions thereof, can be stored in the remote memory/storage device 1150.

The computer 1102 is operable to communicate with wired and wireless devices or entities using the IEEE 802 family of standards, such as wireless devices operatively disposed in wireless communication (e.g., IEEE 802.11 over-the-air modulation techniques). This includes at least Wi-Fi (or Wireless Fidelity), WiMax, and Bluetooth® wireless technologies, among others. Thus, the communication can be a predefined structure as with a conventional network or simply an ad hoc communication between at least two devices. Wi-Fi networks use radio technologies called IEEE 802.118 (a, b, g, n, etc.) to provide secure, reliable, fast wireless connectivity. A Wi-Fi network can be used to connect computers to each other, to the Internet, and to wire networks (which may use IEEE 802.3-related media and functions).

The various elements of the devices as previously described with reference to FIGS. 1, 2, 7, and 8 may include various hardware elements, software elements, or a combination of both. Examples of hardware elements may include devices, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof.

While the present disclosure has been illustrated and described in detail in the drawings and foregoing description, the same is to be considered as illustrative and not restrictive in character, it being understood that only the certain embodiments have been shown and described and that all changes, alternatives, modifications and equivalents that come within the spirit of the disclosure are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the present disclosure, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. An apparatus, comprising:

at least one memory; and logic coupled to the at least one memory, the logic to:

receive, as an input, quantitative patient monitoring information associated with a diabetic treatment of a patient, the patient monitoring information comprising at least one of a blood glucose level information, insulin dosage information, or insulin-on-board (IOB) information, generate a graph from the patient monitoring information, the graph comprising a temporal axis identifying historical readings of the patient monitoring information and a dependent axis showing the patient monitoring information for the historical readings, generate an image of at least a portion of the graph, the image comprising at least one digital image of the graph at a region of interest, process the image of the at least a portion of the graph using a computational model to determine, as an output, a predicted blood glucose condition of the patient, the blood glucose condition comprising one or more of a hypoglycemic episode, a hyperglycemic episode, a low blood sugar episode, a high blood sugar episode, or a normal blood sugar episode, the computational model configured based on historical monitoring information graph images to identify features representing an imminent blood glucose condition, and the processing comprising applying a filter to the image of the graph at the region of interest to determine if a trend in the graph at the region of interest matches the features, and administer a medicament with the apparatus based on the determined blood glucose condition.

2. The apparatus of claim 1, the computational model comprising a convoluted neural network (CNN).

3. The apparatus of claim 1, the blood glucose condition comprising a prediction of a future blood glucose level.

4. The apparatus of claim 3, the prediction comprising a level of confidence in the prediction.

5. A computer-implemented method, comprising, via a processor of a computing device:

receiving, as an input, quantitative patient monitoring information associated with a diabetic treatment of a patient, the patient monitoring information comprising at least one of a blood glucose level information, insulin dosage information, or insulin-on-board (IOB) information, generating a graph from the patient monitoring information, the graph comprising a temporal axis identifying historical readings of the patient monitoring information and a dependent axis showing the patient monitoring information for the historical readings, generating an image of at least a portion of the graph, the image comprising at least one digital image of the graph at a region of interest, processing the image of the at least a portion of the graph using a computational model to determine, as an output, a predicted blood glucose condition of the patient, the blood glucose condition comprising one or more of a hypoglycemic episode, a hyperglycemic episode, a low blood sugar episode, a high blood sugar episode, or a normal blood sugar episode, the computational model configured based on historical monitoring information graph images to identify features representing an imminent blood glucose condition, and the processing comprising applying a filter to the image of the graph at the region of interest to determine if a trend in the graph at the region of interest matches the features, and administering a medicament with an apparatus based on the determined blood glucose condition.

6. The method of claim 5, the computational model comprising a convoluted neural network (CNN).

7. The method of claim 5, the blood glucose condition comprising a prediction of a future blood glucose level.

8. The method of claim 7, the prediction comprising a level of confidence in the prediction.

* * * * *